(12) United States Patent
Lu et al.

(10) Patent No.: US 9,730,935 B2
(45) Date of Patent: Aug. 15, 2017

(54) TARGETING A NON-CANONICAL NOTCH SIGNALING PATHWAY FOR CANCER TREATMENT

(71) Applicant: The Board of Trustees of the Leland Stanford Junior University, Palo Alto, CA (US)

(72) Inventors: Bingwei Lu, Stanford, CA (US); Kyu-Sun Lee, Daejeon (KR)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 120 days.

(21) Appl. No.: 14/567,834

(22) Filed: Dec. 11, 2014

(65) Prior Publication Data

US 2015/0164896 A1    Jun. 18, 2015

Related U.S. Application Data

(60) Provisional application No. 61/915,889, filed on Dec. 13, 2013.

(51) Int. Cl.
| | |
|---|---|
| *A61K 31/517* | (2006.01) |
| *A61K 31/35* | (2006.01) |
| *A61K 31/5377* | (2006.01) |
| *C12N 15/113* | (2010.01) |
| *G01N 33/50* | (2006.01) |

(52) U.S. Cl.
CPC ............ *A61K 31/517* (2013.01); *A61K 31/35* (2013.01); *A61K 31/5377* (2013.01); *G01N 33/5011* (2013.01)

(58) Field of Classification Search
None
See application file for complete search history.

(56) References Cited

U.S. PATENT DOCUMENTS

| | | | |
|---|---|---|---|
| 8,163,499 B2* | 4/2012 | Singh | ................ G01N 33/5011 435/25 |
| 2008/0161260 A1* | 7/2008 | Rahman | ................ C07K 16/44 514/44 R |

OTHER PUBLICATIONS

Martin et al. Cancer Research 2011, vol. 71, pp. 1836-1848.*
Berthier et al. Human Pathology 2011, vol. 42, pp. 75-87.*
Guo et al. Thoracic Cancer 2014, vol. 5, pp. 473-486.*
Allenspach, Eric J. et al., Notch Signaling in Cancer, Cancer Biology & Therapy 1:5, pp. 466-476, Sep./Oct. 2002; © 2002 Landes Bioscience.
Guitierrez, Alejandro et al., High frequency of PTEN, P13K, and AKT abnormalities in T-cell acute lymphoblastic leukemia, blood, 2009 114: pp. 647-650, pre-published online May 20, 2009, American Society of Hematology, US.
Guitierrez, Alejandro et al., NOTCH and P13K-AKT Pathways Intertwined, Cancer Cell Nov. 12, 2007 © 2007 Elsevier Inc., pp. 411-413.
Lee, Keunwook et al., Vital Roles of mTOR complex 2 in Notch-driven thymocyte differentiation and leukemia, J. Exp. Med. vol. 209 No. 4, pp. 713-728, The Rockefeller University Press, Published Apr. 2, 2012.
Meurette, Olivier et al., Notch Activation Induces Akt Signaling via an Autocrine Loop to Prevent Apoptosis in Breast Epithelial Cells, Cancer Research 2009;69: pp. 5015-5022, published Online First Jun. 2, 2009, American Association for Cancer.
Weng, Andrew P. et al., Activating Mutations of NOTCH1 in Human T Cell Acute Lymphoblastic Leukemia, Science, vol. 306, Oct. 8, 2004, pp. 269-271.

* cited by examiner

*Primary Examiner* — Tracy Vivlemore
(74) *Attorney, Agent, or Firm* — Bret E. Field; Bozicevic, Field & Francis LLP

(57) ABSTRACT

Methods and compositions are provided for treating an individual having cancer. Aspects of the methods include administering to the individual an inhibitor of a non-canonical Notch signaling pathway gene in an amount effective to treat the cancer. Also provided are reagents, devices and kits thereof that find use in practicing the subject methods.

23 Claims, 14 Drawing Sheets

(14 of 14 Drawing Sheet(s) Filed in Color)

TARGETING A NON-CANONICAL NOTCH SIGNALING PATHWAY FOR CANCER TREATMENT

GOVERNMENT RIGHTS

This invention was made with government support under contract Nos. NS043167 and AR054926 awarded by the National Institutes of Health. The Government has certain rights in the invention.

FIELD OF THE INVENTION

This invention pertains to the treatment of cancer.

BACKGROUND OF THE INVENTION

Maintaining a delicate balance between self-renewal and differentiation is a hallmark of all stem cells (Doe, 2008; Morrison and Kimble, 2006; Zhong and Chia, 2008). Impairments of such balance can lead to lineage depletion or tumorigenesis. Therapeutic agents that restore this balance, or alternatively that inhibit proteins that promote the imbalance, will find use in treating cancer. The present invention addresses these issues.

SUMMARY OF THE INVENTION

Methods and compositions are provided for treating an individual having cancer. Aspects of the methods include administering to the individual an inhibitor of a non-canonical Notch signaling pathway gene in an amount effective to treat the cancer. Also provided are reagents, devices and kits thereof that find use in practicing the subject methods.

BRIEF DESCRIPTION OF THE DRAWINGS

The invention is best understood from the following detailed description when read in conjunction with the accompanying drawings. The patent or application file contains at least one drawing executed in color. Copies of this patent or patent application publication with color drawing(s) will be provided by the Office upon request and payment of the necessary fee. It is emphasized that, according to common practice, the various features of the drawings are not to-scale. On the contrary, the dimensions of the various features are arbitrarily expanded or reduced for clarity. Included in the drawings are the following figures.

Figure 5:
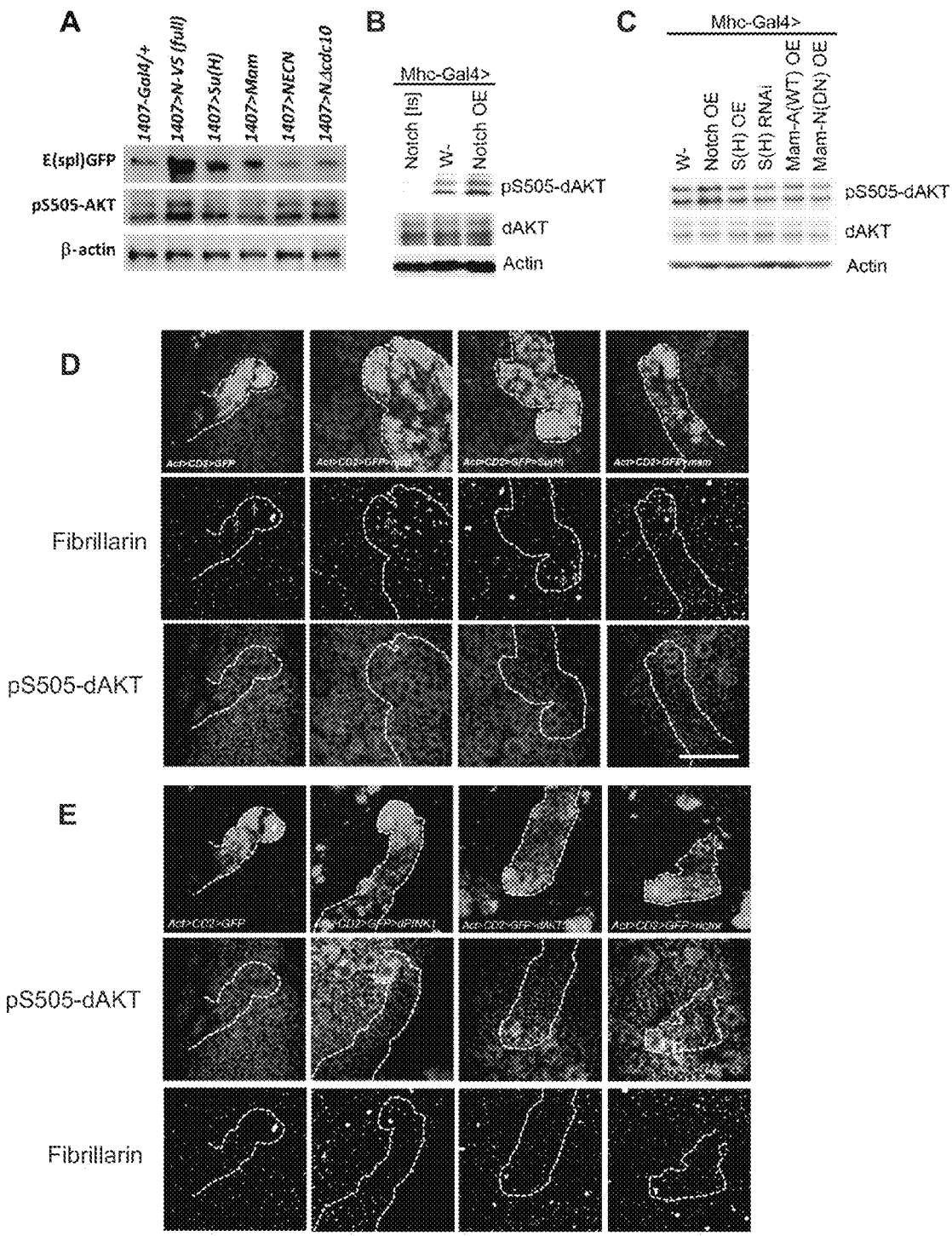

FIG. 5. N regulates mTORC2 activity, but not through the canonical N signaling pathway. (A) Western blot analysis showing that the expression level of the E(spl)-GFP, a reporter of canonical N signaling, was increased in transgenic larval brain overexpressing N, Su(H), or Mam, but not when deletion mutants of N defective in canonical N signaling (NECN and NΔcdc10) were overexpressed. NECN and NΔcdc10 have the entire intracellular domain or the Su(H) interaction sites of N respectively deleted. In contrast, mTORC2 activity as measured by pS505-dAKT level was increased when N, NECN, and NΔcdc10 were overexpressed but not when Su(H), or Mam were overexpressed. 1407-Gal4 was used to express the UAS transgene genes in larval NBs. (B) Western blot analysis showing that the level of pS505-dAKT was decreased in $N^{ts}$ mutant but increased by N–V5 OE. Mhc-Gal4 was used to express N–V5 in muscle tissue. (C) Up- or down-regulation of canonical N pathway genes Su(H) and Mam had no obvious effect on mTORC2 activity in muscle tissue. Total AKT and actin serve as loading controls. (D) Overexpression of canonical N pathway genes promoted nucleolar growth of IP cells but had no effect on mTORC2 activity as measured by pS505-dAKT immunosignals. (E) Activation of the non-canonical N pathway increases mTORC2 activity, but has no obvious effect on nucleolar growth in IP cells. FRT-FLP induced single type II NB clones overexpressing the indicated genes were marked with GFP (green), with their nucleolar size and mTORC2 activation status monitored by Fibrillarin (red) and pS505-dAKT (blue) immunostaining, respectively. Arrows point to the nucleoli of IPs located within the clones. Clones are outlined with white dashed lines.

Figure 6:
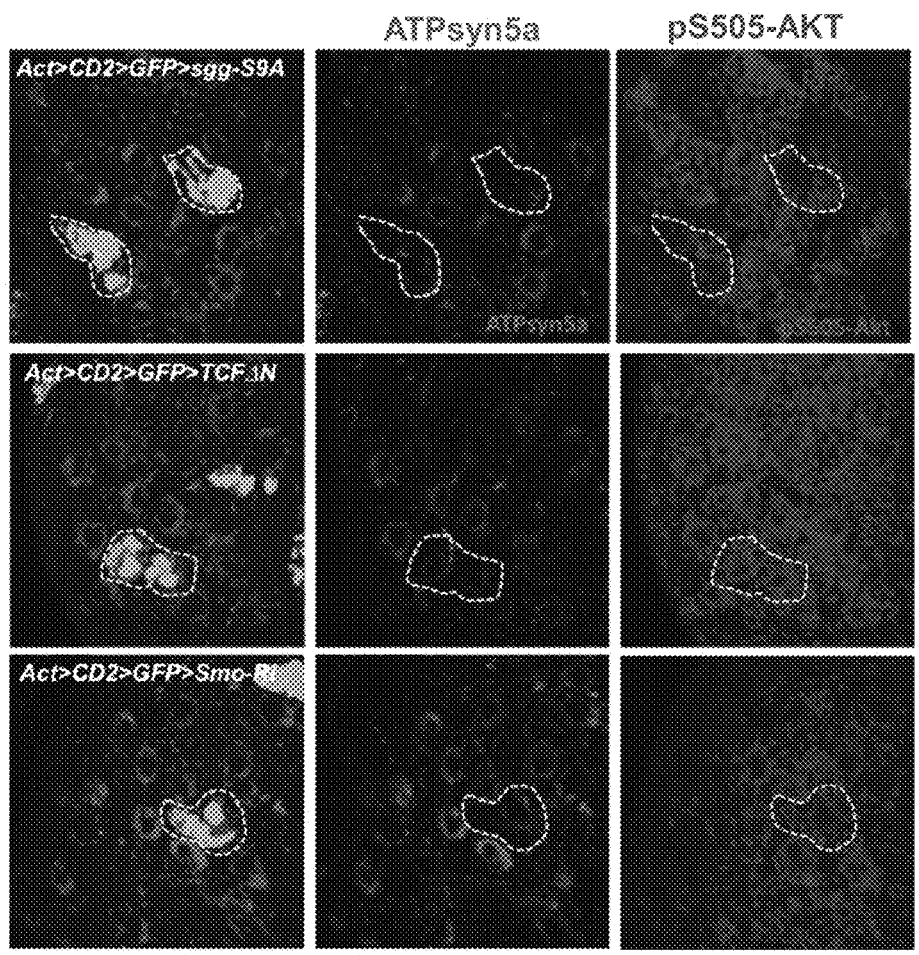

FIG. 6. mTORC2 activity is not changed by Wingless or Hh signaling pathway. FRT-FLP based clonal analysis showing that manipulating the activities of Wingless pathway (sgg-S9A or TCFDN overexpression) or Hedgehog pathway (Smoothened RNAi) had no obvious effect on mTORC2 activity as measured by pS505-dAKT immunosignals. Single type II NB clones were marked with GFP (green).

Figure 1:
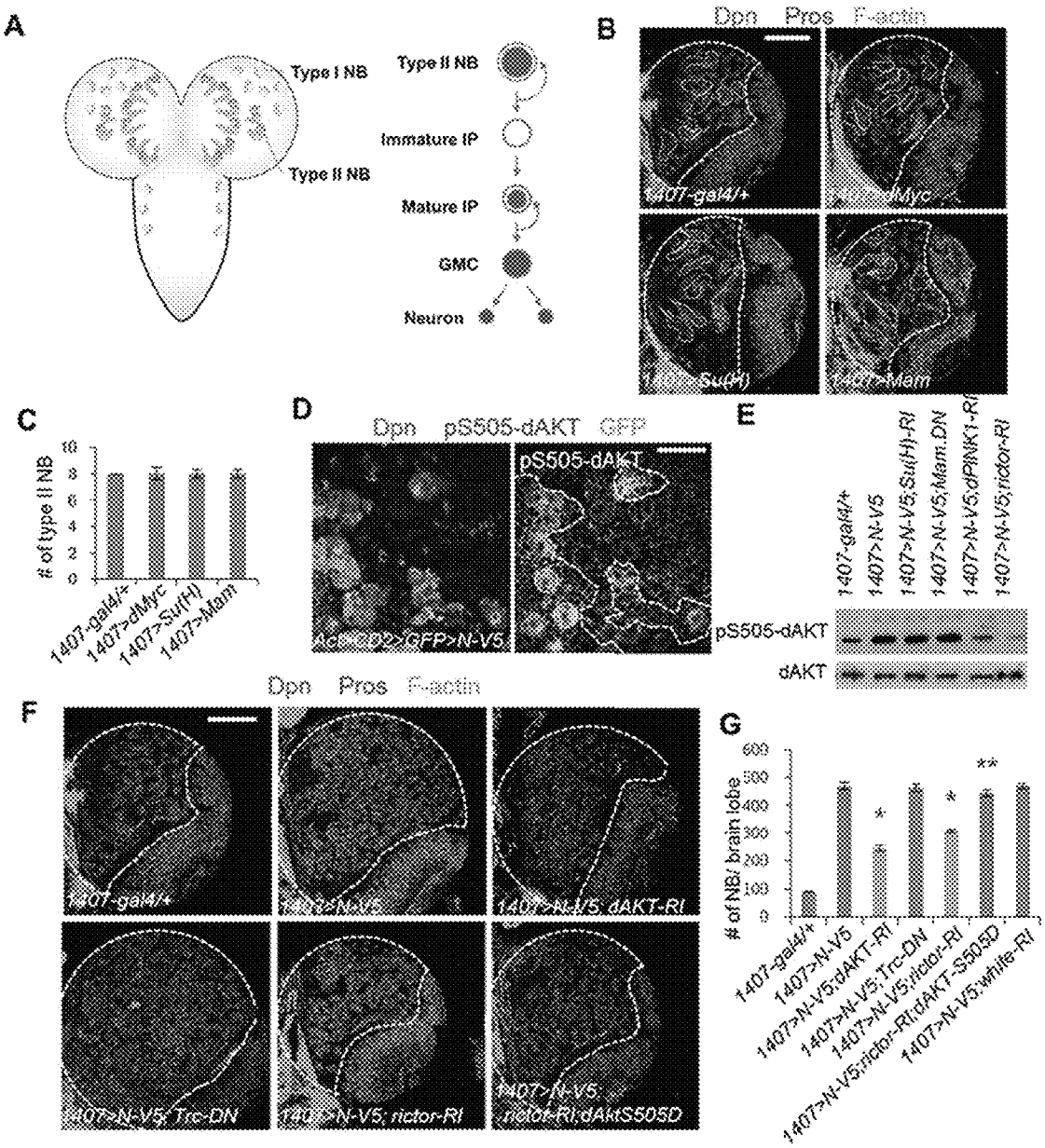
FIG. 1. Notch regulates the mTORC2/AKT pathway in NBs. (A) Diagram of *Drosophila* larval CNS showing type I and type II NBs in the central brain area (left) and the lineage hierarchy of type II NBs (right). (B) The effects of NB-specific overexpression of canonical Notch pathway components Su(H), Mam, or dMyc. Larval brains at 120 h after larval hatching (ALH) were stained for Dpn (NBs), Pros (differentiated cells), and F-actin (cell cortex). Type II NB lineages are marked with fine white lines. In this figure and all subsequent figures, the central brain area is outlined with bold white dashed line, and the Dpn+ NBs within this area are quantified. (C) Quantification of data from B. (D) pS505-dAKT staining of GFP-marked NB flip-out clones overexpressing full-length N (N–v5). NBs within clones (yellow circled) show increased pS505-AKT signal than those outside of clones (red circled). (E) Assay of mTORC2 activity by pS505-dAKT western blot (WB) analysis of larva brain extracts after RNAi (RI) or dominant-negative (DN) transgene expression. Total dAKT as loading control. (F) N-induced NB expansions is blocked by inhibition of key components of mTORC2/AKT pathway, and the effect of Rictor inhibition is restored by AKT-S505D but not Trc-DN. (G) Quantification of data from E. *, p<0.0003 (vs. 1407>N–V5/+),**, p<0.002 (vs. 1407>N–V5; rictor-RI) in Student's t-test; n=10. Scale bars, 100 µm (A, E); 20 µm (C).
Figure 4:
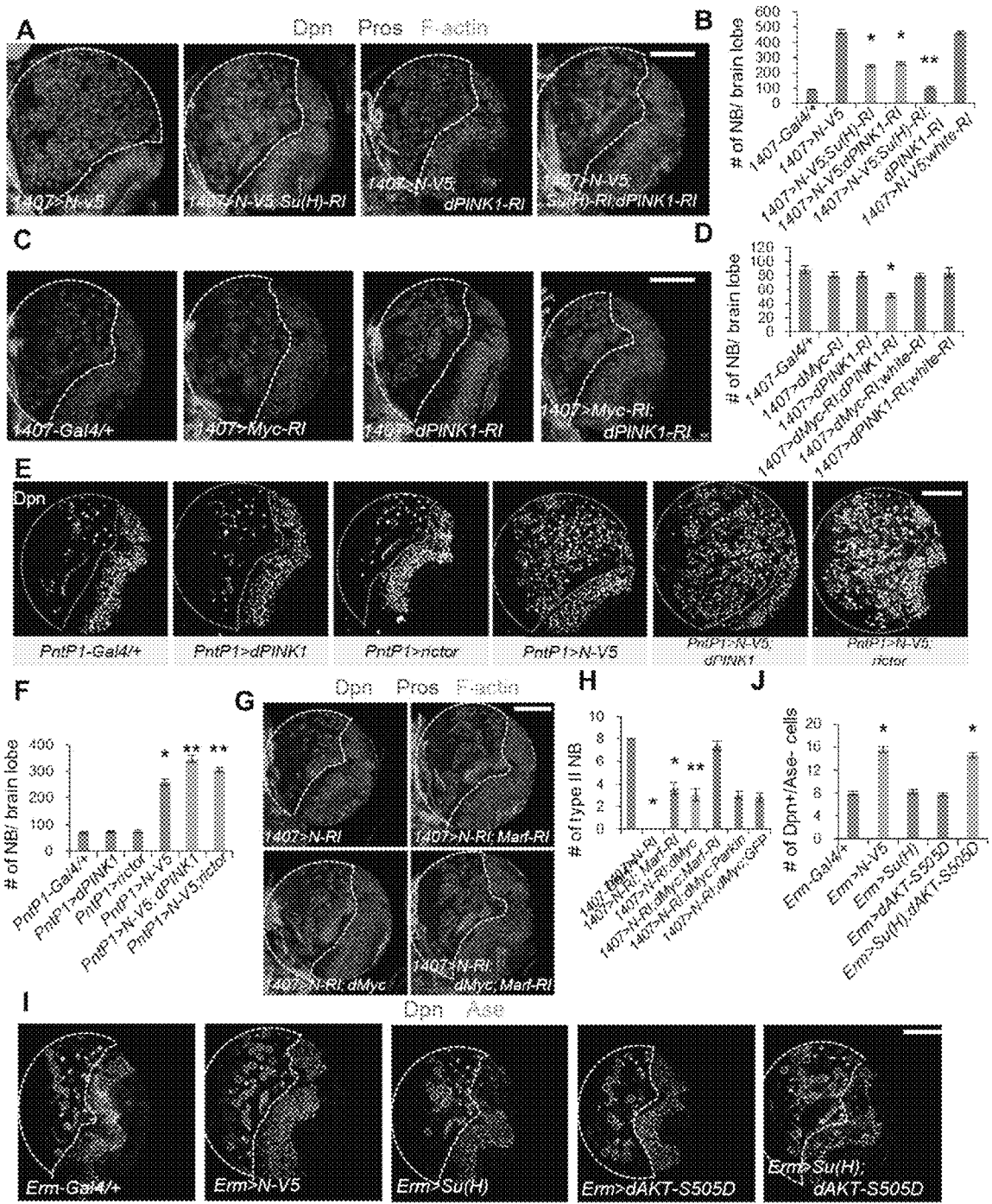
FIG. 4. Interaction between canonical and non-canonical N signaling on NB homeostasis. (A) Effects of combined RNAi of Su(H) and PINK1 on N GOF-induced NB expansion. (B) Quantification of data from A.*, p<0.0002 vs. 1407>N–V5/+; **, p<0.0005 vs. 1407>N–V5; Su(H)-RI or 1407>N–V5; dPINK1-RI, n=5. (C) Effects of combined RNAi of Myc and PINK1 on normal NB number. (D) Quantification of data from C. *, p<0.001 vs. 1407>dMyc-RI or 1407>dPINK1-RI; n=5. (E) Effects of co-expression of PINK1 and Rictor on N GOF-induced NB expansion. (F) Quantification of data from E. *, p<0.0001 vs. PntP1-Gal4/+ control; **, p<0.05 vs. PntP1>N–V5/+; n=5. (G) Synergy between dMyc-OE and Marf-RI in rescuing N LOF-induced type II NB loss. (H) Quantification of data from G. *, p<0.005 vs. 1407>N–RI/+;**, p<0.05 vs. 1407>N–RI; dMyc or 1407>N–RI; Marf-RI; n=5. Parkin or GFP co-expression serves as specificity control. (I) Effects of co-expression of Su(H) and dAKT-S505D in mature IPs (driven by Erm-gal4). The ectopic NBs dedifferentiated from mature IPs are identified by marker expression (Dpn+ and Ase–) and marked by white dashed circles. (J) Quantification of data from I. *, p<0.0002 vs. Erm-Gal4/+ control in Student's t-test; n=5. Scale bars, 100 µm.
Figure 7:
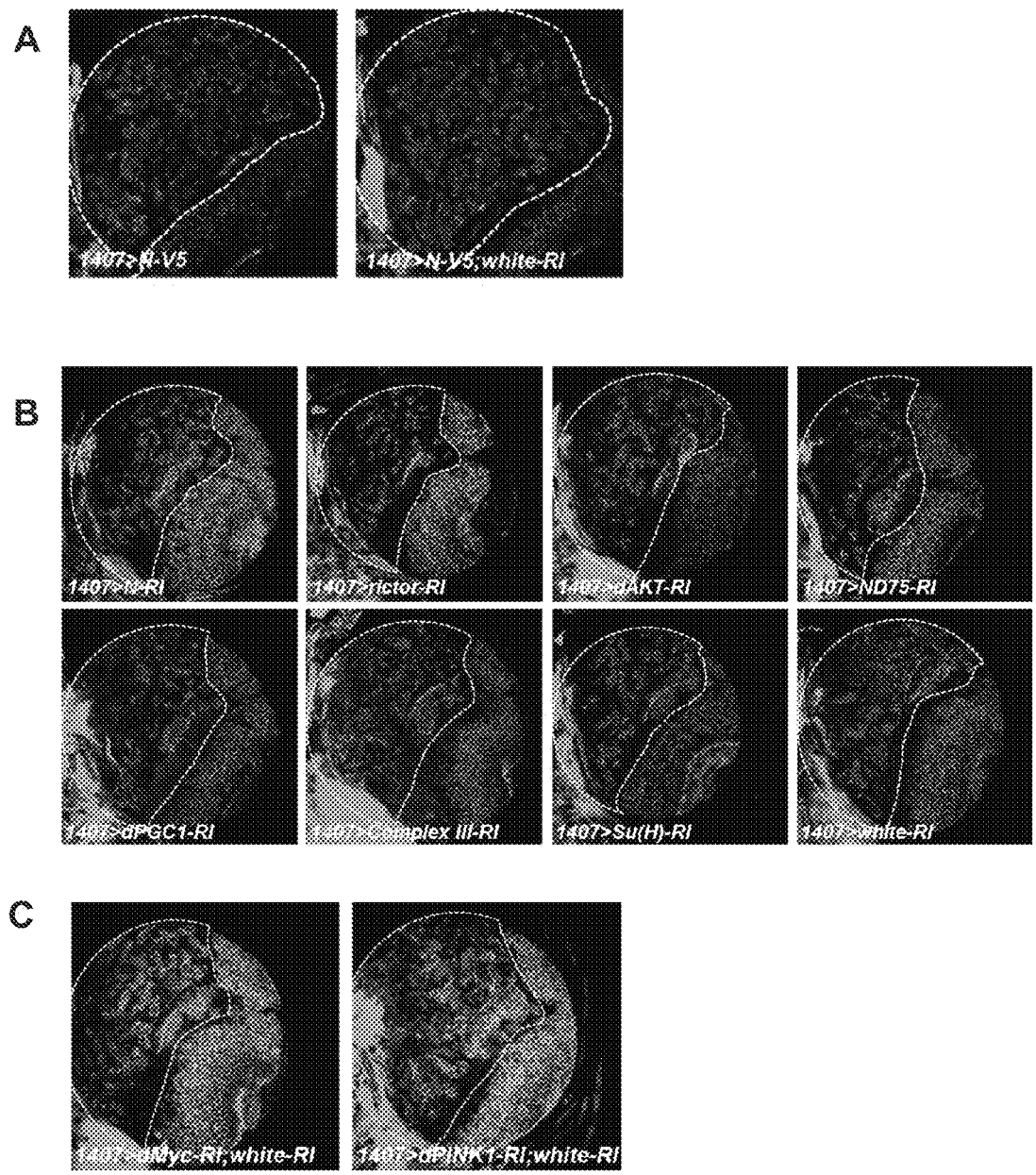

FIG. 7. Effect of RNAi mediated knockdown of the N pathway-related genes on larval central brain neuroblast maintenance and control experiments using white (W) RNAi. (A) N overexpression-induced NB overproliferation was not altered by the co-expression of the control W RNAi. Data quantification is shown in FIGS. 1G and 4B. (B) Effects of RNAi of the indicated N pathway-related genes on NB number. Transgenes were driven by the NB-specific 1407-Gal4. Larval brains at 120 h AHL were stained for Dpn (NBs), Pros (differentiated cells), and F-actin (cell cortex). (C) Control experiments showing that the combination of W RNAi with Myc- or PINK1-RNAi did not change central brain NB number. Data quantification is shown in FIG. 4D.

Figure 8:
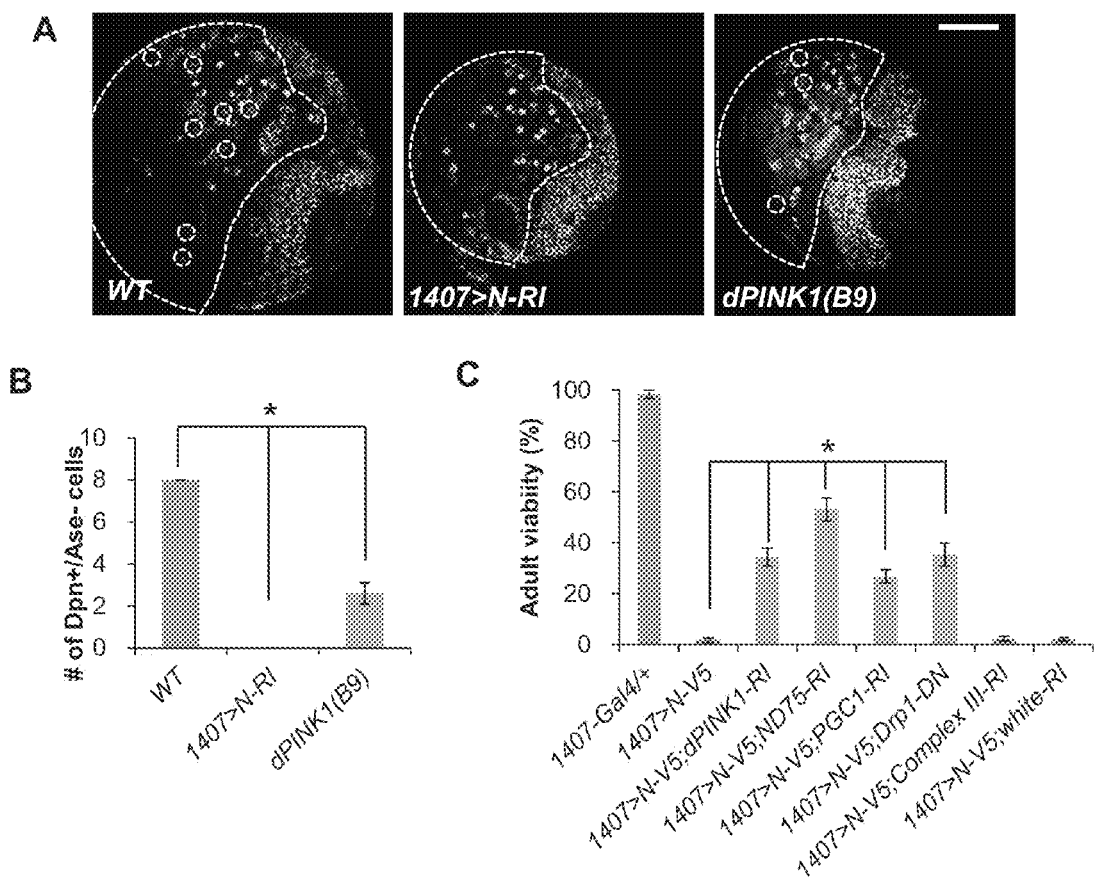

FIG. 8. Effect of PINK1 inhibition on normal NB maintenance and on N overexpression induced lethality. (A) The number of type II NBs (Dpn-positive and Ase– negative cells) was significantly reduced in $dPINK1^{B9}$ null mutant background. Dpn: red; Ase: Green. WT and 1407-Gal4>N–RI brains were used as controls. (B) Quantification of data from A. *, p<0.005 versus WT control; n=5. (C) Effects of manipulating mitochondria-related genes, including PINK1, on the pharate adult lethality phenotype caused by NB-specific N overexpression. *, p<0.001 versus 1407>N–V5; n=5.

Figure 9:
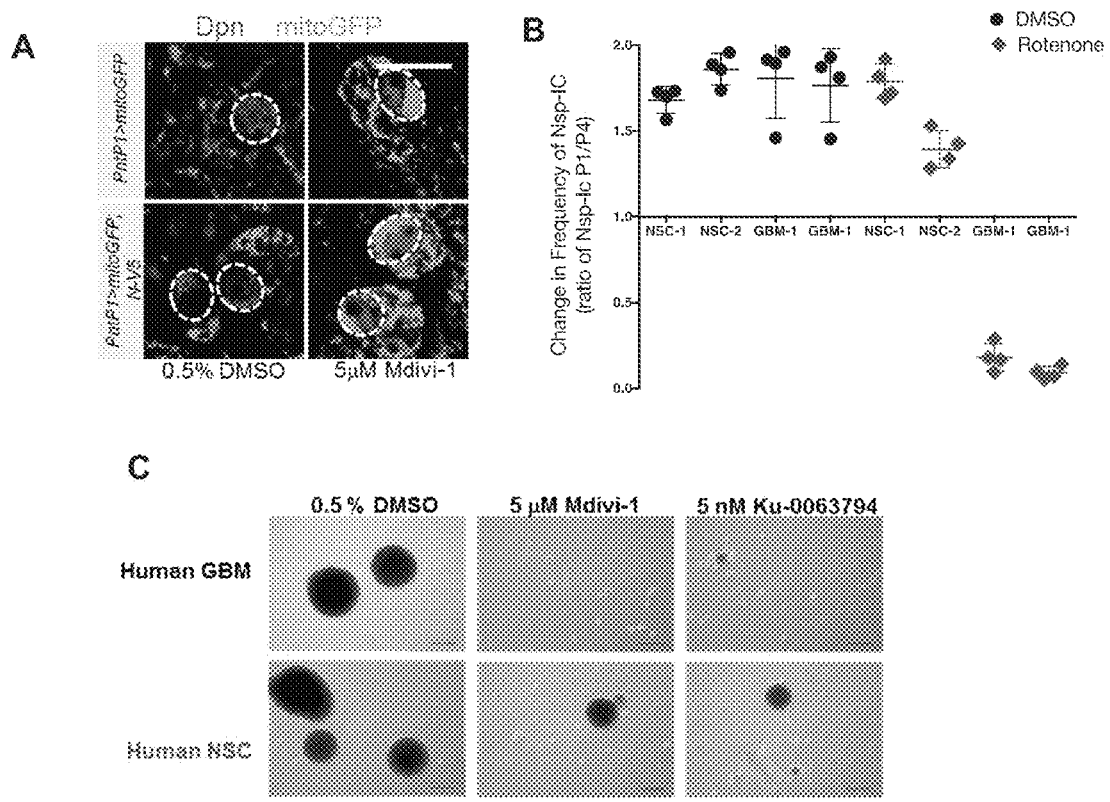

FIG. 9. Effects of pharmacological inhibition of Drp1 (Mdivi-1), RCC-I (rotenone), and mTOCR2 (Ku-0063794) on mitochondrial morphology of Drosophila type II NBs and on the self-renewal of human NSC and GBM CSCs. (A) Mitochondrial morphology of Drosophila type II NBs from animals treated with vehicle (0.5% DMSO) or 5 µM Drp1 inhibitor Mdivi-1. Mitochondria are visualized using genetically-encoded mitoGFP (green). NBs are marked with Dpn (red) and outlined with white circles. Scale bars, 20 µm. (B), Effect of rotenone (10 nM) on the number of self-renewing cells (neurosphere initiating cells, Nsp-IC) of two human NSC and two GBM cell lines at passage 1 versus passage 4. DMSO serves as vehicle control. (C) Representative bright field images of human GBM and NSC neurospheres. Dissociated single cells from human GBM sample or fetal forebrain tissue were plated at 100 cells/well and treated with DMSO vehicle control, or pharmacological inhibitors of Drp1 (Mdivi-1, 5 µM) or mTORC2 (Ku-0063794, 5 nM). Scale bar, 100 µm.

Figure 10:
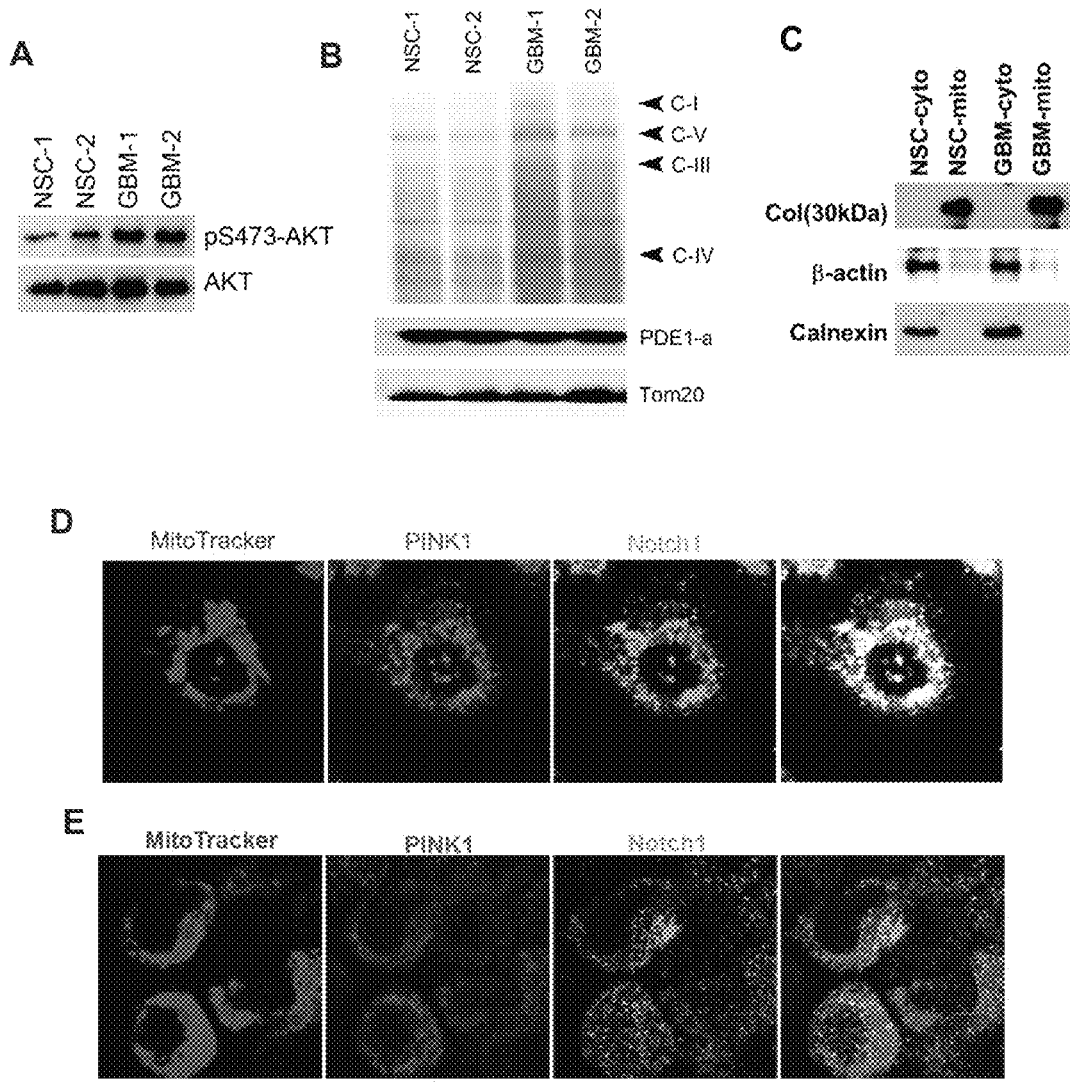

FIG. 10. Biochemical and immunohistochemical analyses of human NSC and GBM cells. (A) Western blot analysis showed that mTORC2 activity as measured by p-5473-AKT level was increased in human GBM compared to NSC culture. (B) Blue native gel (BNG) analysis showing increased RCC assembly in human GBM compared to normal NSC. PDE1-a and Tom20 serve as loading controls of mitochondrial fraction. (C) Western blot analysis showing that purified mitochondria from NSCs and GBM cells were not contaminated by other membranous organelles such as the ER. Calnexin and complex I 30 kDa serve as ER and mitochondrial markers, respectively. (D, E) Immunostaining of hNotch1 (green) and PINK1 (red), showing their co-localization on mitochondria (marked with MitoTracker, blue) in human HEK293 cells (D) and GBM cells (E). Scale bar; 30 µm.

Figure 11:
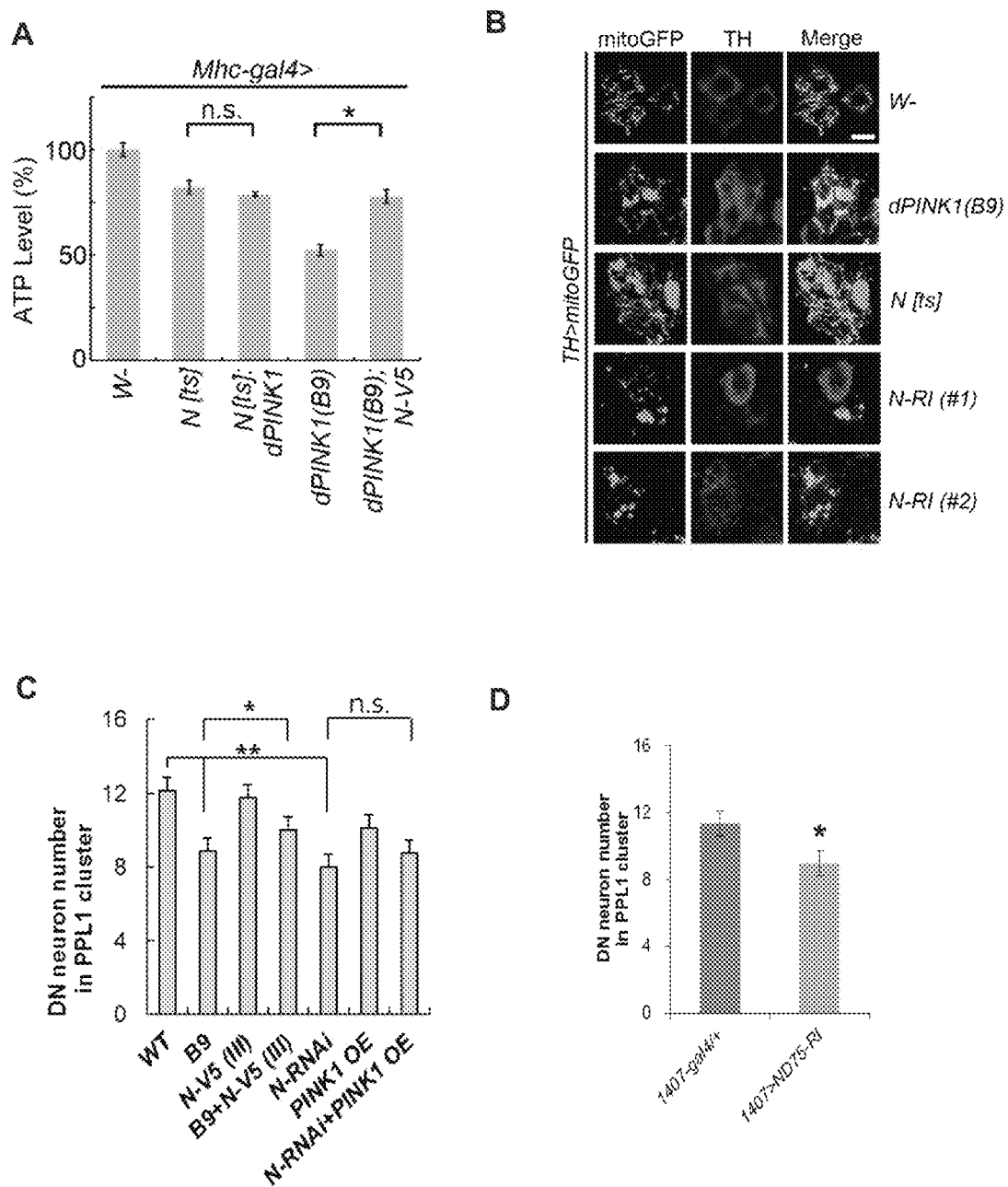

FIG. 11. Analyses of Mitochondrial function, morphology and DA neuron number in N and PINK1 mutant background. (A) Reduction of thoracic muscle ATP production caused by PINK1 LOF was rescued by N GOF, whereas the ATP reduction caused by N LOF was not rescued by PINK1 GOF. (B) Effects of N LOF on mitochondrial morphology in dopaminergic neurons (DNs). N inhibition as in $N^{ts}$ mutant or by TH-Gal4-driven N RNAi caused mitochondrial aggregation in TH-positive DNs, similar to that seen in dPINK1 (B9) mutant. Scale bar, 5 µm. (C) Genetic interaction between N and PINK1 in regulating DN maintenance. TH-Gal4 driven N RNAi caused loss of DNs in the PPL1 cluster, similar to that seen in dPINK1(B9) mutant. PINK1-OE failed to rescue N RNAi effect, whereas N-OE partially rescued dPINK1(B9) mutant effect on DN number. *, p<0.05. ** p<0.01 versus TH-Gal4/+ control in Student's t-test. (D) NB-specific knockdown of ND75 resulted in loss of DA neurons in surviving adults. *, p<0.0001 versus 1407-Gal4 control.

Figure 12:
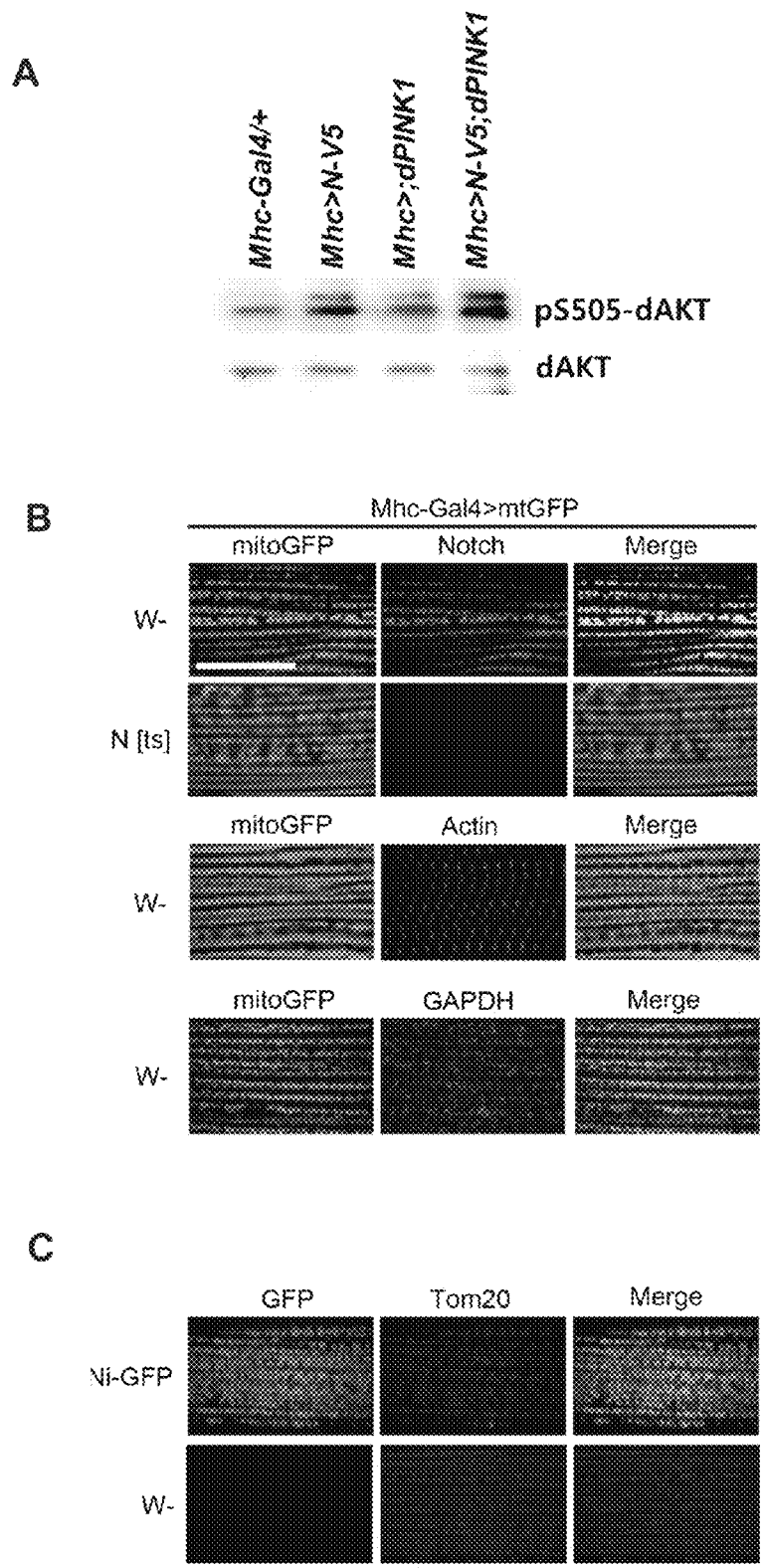

FIG. 12. Characterization of the mitochondrial localization of Drosophila N and the additive effects of N and PINK on mTORC2/AKT activity. (A) Western blot analysis showing that the level pS505-dAKT was increased in either N GOF or PINK1 GOF condition. The co-expression of N and PINK resulted in further increase of mTORC2/AKT activity compared with overexpression of either gene alone. Mhc-Gal4 was used to express UAS transgenes in muscle tissue. (B) Immunohistochemical analysis showing endogenous N co-localization with the mito-GFP reporter in thoracic muscle. The Notch immunosignal on mitochondria completely disappeared in N$^{ts}$ mutant. Other cytosolic markers, such as Actin and GAPDH, did not co-localize with the mitoGFP reporter. (C) GFP-tagged Notch (NiGFP) expressed from the endogenous N locus showed co-localization with the mitochondrial marker Tom20 in thoracic muscle tissue. Scale bar; 30 μm.

Figure 13:
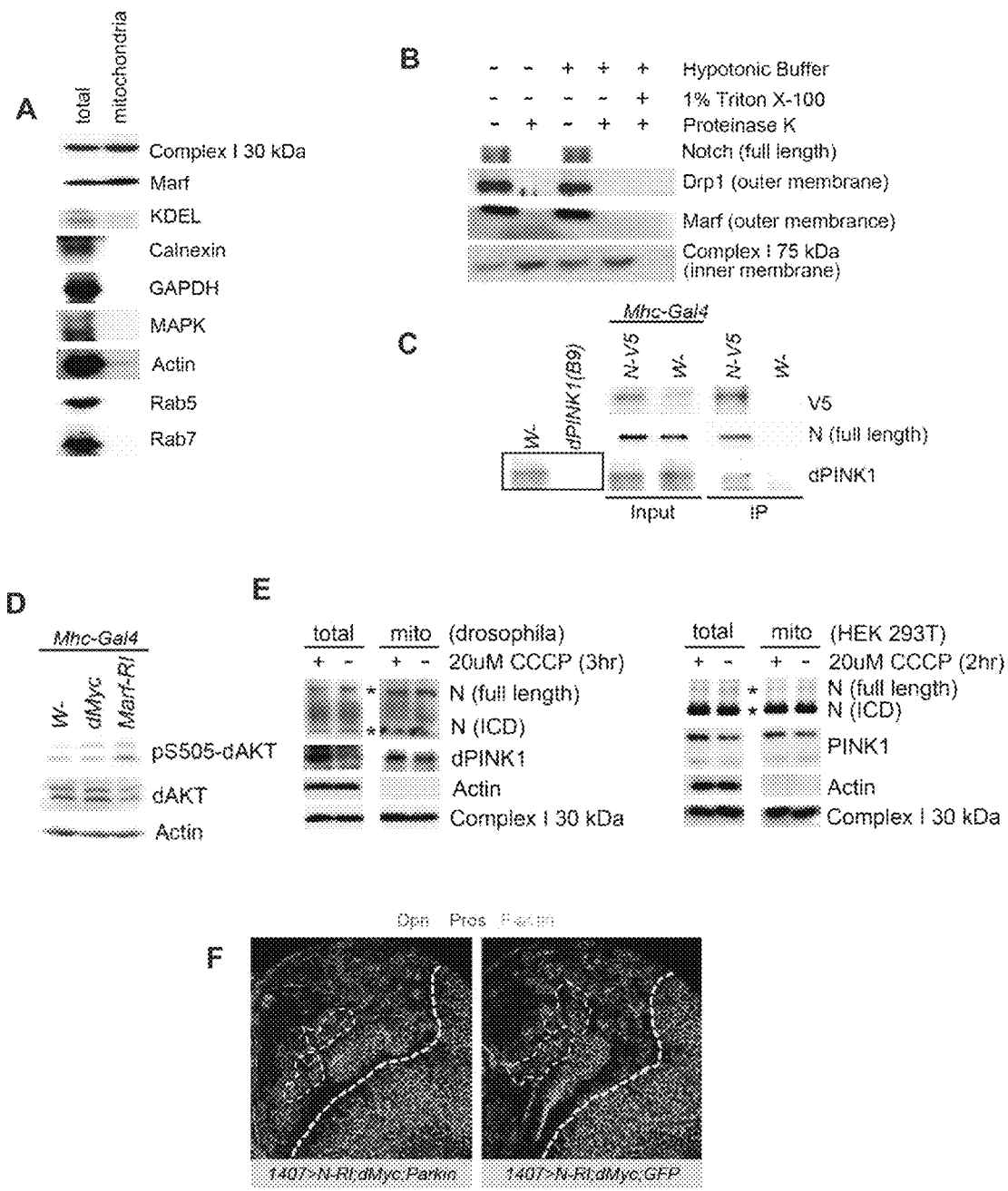

FIG. 13. Additional evidence supporting N-PINK1 interaction. (A) Western blot analysis showing that Percoll-gradient purified mitochondria were not contaminated by other membranous organelles such as the ER and endosomes and the cytosol. Mitochondrial markers: complex I 30 kDa, Marf; ER markers: KDEL, calnexin; endosomal markers: Rab5, Rab7; cytosolic markers: GAPDH, MAPK, Actin. (B) Mitochondrial fractionation assays showing that N behaves similarly as the mitochondrial markers Drp1 and Marf in its localization. Drp1 and Marf serve as outer mitochondrial membrane markers and complex-I 75 kD as inner mitochondrial membrane marker. (C) Co-IP between endogenous PINK1 and overexpressed N in fly muscle extracts. Mhc-Gal4 was used to drive N expression. dPINK1(B9) mutant WB (left) is used to demonstrate antibody specificity. (D) Western blot analysis showing that mTORC2 activity (as measured by pS505-dAKT level) was upregulated in muscle tissues overexpressing UAS-Marf RNAi, but not UAS-dMyc, transgenes. Total AKT and actin serve as loading controls. (E) Western blot analysis showed that the amount of mitochondrial N was not affected by mitochondrial damage reagent CCCP in either Drosophila muscle tissue or HEK 293T cells. Actin and complex I 30 kDa serve as loading controls for total lysate and mitochondrial fraction, respectively. Note that mitochondrial PINK1 level was increased after CCCP treatment in both samples. (F) Control experiments showing that co-expression of Parkin or GFP with dMyc did not alter the ability of dMyc to partially rescue N RNAi-induced type II NB loss. 1407>N–RI; dMyc; GFP or 1407>N–RI, dMyc; Parkin larval brains were immunostained for NBs (Dpn), differentiated cells (Pros), and cell cortex (F-Actin). Type II NB lineages are outlined. Data quantification is shown in FIG. 4H. Scale bar; 100 μm.

Figure 14:
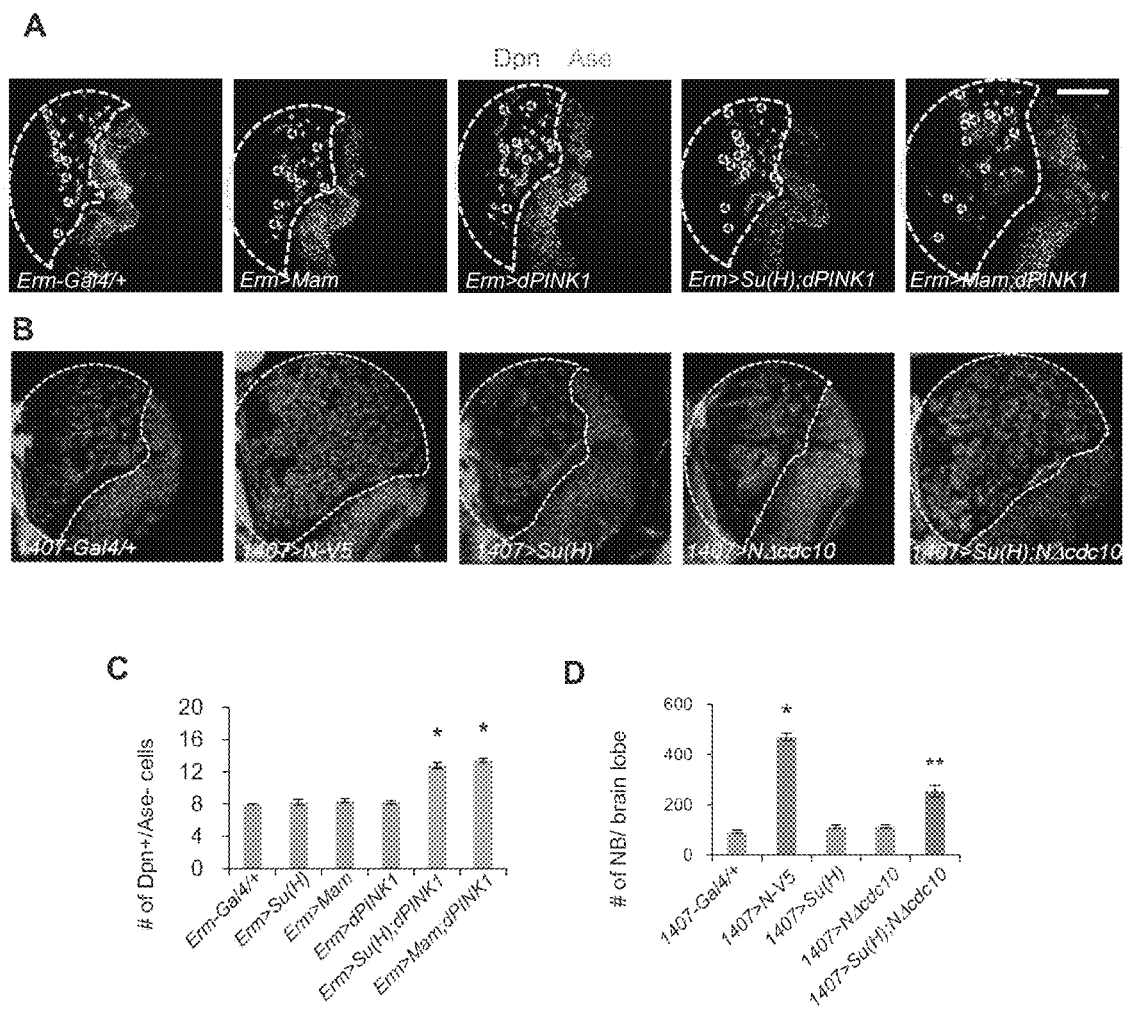

FIG. 14. Further evidence supporting the interaction between canonical and non-canonical Notch signaling on NB homeostasis. (A) Combined overexpression of canonical Notch pathway component, Su(H) or Mam, with non-canonical Notch pathway component, dPINK1, specifically in mature IPs led to the formation of ectopic type II NBs. Ectopic type II NBs (Dpn-positive and Ase-negative) are marked with white dashed circles. (B) Combined overexpression of Su(H) and NΔcdc10 also induced ectopic NBs like as in N overexpression case. Larval brains were immunostained for NBs (Dpn), differentiated cells (Pros), and cell cortex (F-Actin). (C) Quantification of data from A. *, p<0.001 versus Erm-Gal4/+ control; n=5. (D) Quantification of data from B. *, p<0.001 versus 1407-Gal4/+ control; **, p<0.001 versus 1407>Su(H) or 1407>NΔcdc10; n=5. Scale bar; 100 μm.

DETAILED DESCRIPTION OF THE INVENTION

Methods and compositions are provided for treating an individual having cancer. Aspects of the methods include administering to the individual an inhibitor of a non-canonical Notch signaling pathway gene in an amount effective to treat the cancer. Also provided are reagents, devices and kits thereof that find use in practicing the subject methods. These and other objects, advantages, and features of the invention will become apparent to those persons skilled in the art upon reading the details of the compositions and methods as more fully described below.

Before the present methods and compositions are described, it is to be understood that this invention is not limited to particular method or composition described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

It must be noted that as used herein and in the appended claims, the singular forms "a", "an", and "the" include plural referents unless the context clearly dictates otherwise. Thus, for example, reference to "a cell" includes a plurality of such cells and reference to "the peptide" includes reference to one or more peptides and equivalents thereof, e.g. polypeptides, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Methods and compositions are provided for reducing cancer cell proliferation, e.g. in an individual having a cancer, e.g. so as to treat the cancer. By cancer it is meant the group of diseases involving unregulated cell growth. In cancer, cells proliferate, i.e. divide, uncontrollably, forming malignant tumors, and invading nearby parts of the body. The cancer may also metastasize, that is, spread to more distant parts of the body through the lymphatic system or bloodstream. By "treatment", "treating" and the like it is generally meant obtaining a desired pharmacologic and/or physiologic effect. The effect may be prophylactic in terms of completely or partially preventing a cancer or symptom thereof and/or may be therapeutic in terms of a partial or complete cure for a cancer and/or adverse effect attributable to the cancer. "Treatment" as used herein covers any treatment of a cancer in a mammal, and includes: (a) preventing the cancer from occurring in a subject which may be predisposed to the cancer but has not yet been diagnosed as having it; (b) inhibiting the cancer, i.e., arresting its development; or (c) relieving the cancer, i.e., causing regression of the cancer. The therapeutic agent may be administered before, during or after the onset of cancer. The treatment of ongoing cancer, where the treatment stabilizes or reduces the undesirable clinical symptoms of the patient, is of particular interest. Such treatment is desirably performed prior to complete loss of function in the affected tissues. The subject therapy will desirably be administered during the symptomatic stage of the cancer, and in some cases after the symptomatic stage of the cancer. The terms "individual," "subject," "host," and "patient," are used interchangeably herein and refer to any mammalian subject for whom diagnosis, treatment, or therapy is desired, particularly humans. In some instances, the subject methods and compositions reduce e.g. inhibit, the proliferation of the cancer. In some instances, the subject methods and compositions reduce, e.g. inhibit, the metastasis of the cancer.

In some embodiments, the cancer is a Notch-associated cancer; that is, the cancer is associated with, i.e., due at least in part to, active Notch signaling. By "Notch" it is meant the evolutionarily conserved single-pass transmembrane receptor that affects numerous cell fate decisions through short-range cell-cell interactions. Notch protein (cLIN-12 and cGLP-1 in *C. elegans*, Notch in *Drosophila*, Notch1-4 in mammals) consists of an extracellular domain (NECD) with 29-36 epidermal growth factor (EGF) repeats for ligand binding, a transmembrane domain (TM), and an intracellular domain (NICD) having transcriptional activity. By "active Notch signaling", it is meant that the Notch protein is active in the cancer cell, e.g. it is an activated Notch, or a constitutively active Notch, e.g. the Notch protein has been mutated such that the Notch protein or a domain thereof is always active. Examples of Notch-associated cancers include hematological malignancies, e.g. acute lymphoblastic leukemia (T-ALL); mammary gland tumors, e.g. breast cancer; brain tumors, e.g. glioblastoma multiforme (GBM); lung cancer; and intestinal cancer. A cancer may be readily identified as a Notch-associated cancer by detecting in a cancerous cell, e.g. in a tumor biopsy or cell smear, a Notch mutation that results in constitutively active Notch. A number of mutations have been identified that result in constitutively active Notch signaling, which may be detected by, for example, chromosome spread or PCR as known in the art. Alternatively, a cancer may be identified as a Notch-associated cancer by detecting the upregulated activity of downstream effectors of Notch signaling, e.g. the upregulated activity of the non-canonical Notch signaling proteins disclosed herein, e.g. elevated N and PINK1 expression (FIG. 3K), elevated mTORC2 signaling (increased Akt phosphorylation) (FIG. 10A), and elevated respiratory chain complex assembly (FIG. 10B) as compared to noncancerous cells.

In some aspects of the subject methods, a cancer cell, e.g. a Notch-associated cancer cell, i.e. a cancer cell whose cancerous state is associated with active Notch, is contacted with an inhibitor, or antagonist, of a non-canonical Notch signaling gene in an amount effective to modulate cancer cell proliferation. By an inhibitor, or antagonist, it is meant an agent that antagonizes, inhibits, suppresses, or negatively regulates the expression or activity of a non-canonical Notch signaling pathway gene. By a non-canonical Notch signaling pathway gene, it is meant a gene whose protein product mediates non-canonical Notch signaling in a cell.

Notch protein modulates cell activity by a canonical pathway and non-canonical pathways. In canonical Notch pathway signaling, Notch ligands (transmembrane proteins comprising three motifs: DSL (Delta, Serrate, LAG-2), DOS (Delta and OSM-11 like) and EGF repeats) bind to the EGF repeats of the Notch extracellular domain from adjacent cells. The ligand-Notch interaction allows members of the α-secretase/metalloprotease family (ADAM10/Kuzmanian, ADAM17/TACE) to cleave the extracellular domain of Notch, leading to sequential cytoplasmic cleavage of the intracellular domain of Notch by γ-secretase (a multi-subunit protease complex composed of presenilin (PS), nicastrin (NCT), Aph-1, Pen-2 and others). The freed intracellular domain translocates to the nucleus, where it interacts via its RAM domain with the DNA-binding transcription factor CSL ("CBF1/RBPjk" in vertebrates, "Suppressor of Hairless" in *Drosophila*, "Lag-1" in *C. elegans*) and acts as a co-activator for CSL, Mastermind-like proteins ("MAML1" in vertebrates, "Mastermind" in *drosophila*, "Lag-3" in *C. elegans*) and other cofactors such as CBP/p300 to transcriptionally activate Notch target genes. In the absence of free intracellular domain Notch, CSL functions as a sequence-specific repressor. Thus, genes that mediate canonical Notch signaling (that is, "canonical Notch signaling genes") would include genes encoding polypeptides of the γ-secretase complex, CSL ("CBF1/RBPjk" in vertebrates, "Suppressor of Hairless" in *Drosophila*, "Lag-1" in *C. elegans*), genes encoding Mastermind-like proteins ("MAML1" in vertebrates, "Mastermind" in *drosophila*, "Lag-3" in *C. elegans*) and the CBP/p300 gene.

Notch can also signal through non-canonical pathways. Non-canonical Notch signaling is CSL-independent and can be either ligand-dependent or independent. Although some genes are affected by non-canonical Notch function, in most cases the mediators of non-canonical Notch signaling are unknown (summarized in Table 1). The most well studied and conserved effect of non-canonical Notch function is regulation of Wnt/β-catenin signaling. In this non-canonical Notch signaling pathway, Notch binds and titrate levels of the obligate Wnt-signaling component active β-catenin. Therefore, active β-catenin activity may serve as a useful readout for non-canonical Notch signals. Other studied non-canonical Notch signaling pathways include signaling through NF-kappa B, signaling through the JNK pathway, and signaling through HES1 and MCK.

As disclosed in the working examples, the inventors of the present disclosure have discovered that mTORC2, Akt, and proteins that promote mitochondrial development or function, e.g. mitochondrial quality control proteins, mitochondrial respiratory chain complex proteins, mitochondrial fission proteins, and mitochondrial biogenesis proteins, mediate non-canonical Notch signaling; for example, the mitochondrial quality control gene PTEN-induced putative kinase 1 (PINK1), polypeptides of mitochondrial respiratory chain complex I (RCCI, e.g. the 75 kD subunit ND-75), the mitochondrial fission protein Dynamin-related protein (Drp1), and the mitochondrial biogenesis protein Peroxisome proliferator-activated receptor gamma coactivator 1-alpha (PGC-1α). In other words, the genes encoding these proteins are non-canonical Notch signaling genes. Moreover, as disclosed in the working examples, the inventors of the present disclosure have discovered that these genes mediate Notch-promoted cell proliferation. By contacting a cancer cell with an agent that inhibits the expression or activity of any of these non-canonical Notch signaling genes, Notch-induced cancer cell proliferation is suppressed. Non-limiting examples of agents include, e.g., Mdivi-1 (targeting Drp1), Ku-0063794 (targeting mTOR), or rotenone (targeting mitochondrial complex I), shRNA TRCN7099 (5'-TAGATGAAGCACATTTGC GGC-3' (SEQ ID NO:1) and TRCN7101: 5'-TATCAGATACTCCTCCA-GCCG-3'(SEQ ID NO:2); Open Biosystems) (targeting PINK1).

Agents suitable for inhibiting non-canonical Notch signaling genes in the subject methods include small molecule compounds, e.g. a naturally occurring or synthetic small molecule compound. Naturally occurring or synthetic small molecule compounds of interest include numerous chemical classes, such as organic molecules, e.g., small organic compounds having a molecular weight of more than 50 and less than about 2,500 daltons. Candidate agents comprise functional groups for structural interaction with proteins, particularly hydrogen bonding, and typically include at least an amine, carbonyl, hydroxyl or carboxyl group, preferably at least two of the functional chemical groups. The candidate agents may include cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Exemplary of pharmaceutical agents suitable for this invention are those described in, "The Pharmacological Basis of Therapeutics," Goodman and Gilman, McGraw-Hill, New York, N.Y., (1996), Ninth edition. Also included are toxins, and biological and chemical warfare agents, for example see Somani, S. M. (Ed.), "Chemical Warfare Agents," Academic Press, New York, 1992). Small molecule compounds can be provided directly to the medium in which the cells are being cultured, for example as a solution in DMSO or other solvent.

Agents suitable for inhibiting non-canonical Notch signaling genes in the subject methods also include nucleic acids, for example, nucleic acids that encode siRNA, shRNA or antisense molecules, or nucleic acids that encode polypeptides. Many vectors useful for transferring nucleic acids into target cells are available. The vectors may be maintained episomally, e.g. as plasmids, minicircle DNAs, virus-derived vectors such cytomegalovirus, adenovirus, etc., or they may be integrated into the target cell genome, through homologous recombination or random integration, e.g. retrovirus derived vectors such as MMLV, HIV-1, ALV, etc.

Vectors may be provided directly to the subject cells. In other words, the pluripotent cells are contacted with vectors comprising the nucleic acid of interest such that the vectors are taken up by the cells. Methods for contacting cells with nucleic acid vectors, such as electroporation, calcium chloride transfection, and lipofection, are well known in the art.

Alternatively, the nucleic acid of interest may be provided to the subject cells via a virus. In other words, the pluripotent cells are contacted with viral particles comprising the nucleic acid of interest. Retroviruses, for example, lentiviruses, are particularly suitable to the method of the invention. Commonly used retroviral vectors are "defective", i.e. unable to produce viral proteins required for productive infection. Rather, replication of the vector requires growth in a packaging cell line. To generate viral particles comprising nucleic acids of interest, the retroviral nucleic acids comprising the nucleic acid are packaged into viral capsids by a packaging cell line. Different packaging cell lines provide a different envelope protein to be incorporated into the capsid, this envelope protein determining the specificity of the viral particle for the cells. Envelope proteins are of at least three types, ecotropic, amphotropic and xenotropic. Retroviruses packaged with ecotropic envelope protein, e.g. MMLV, are capable of infecting most murine and rat cell types, and are generated by using ecotropic packaging cell lines such as BOSC23 (Pear et al. (1993) P.N.A.S. 90:8392-8396). Retroviruses bearing amphotropic envelope protein, e.g. 4070A (Danos et al, supra.), are capable of infecting most mammalian cell types, including human, dog and mouse, and are generated by using amphotropic packaging cell lines such as PA12 (Miller et al. (1985) Mol. Cell. Biol. 5:431-437); PA317 (Miller et al. (1986) Mol. Cell. Biol. 6:2895-2902); GRIP (Danos et al. (1988) PNAS 85:6460-6464). Retroviruses packaged with xenotropic envelope protein, e.g. AKR env, are capable of infecting most mammalian cell types, except murine cells. The appropriate packaging cell line may be used to ensure that the subject CD33+ differentiated somatic cells are targeted by the packaged viral particles. Methods of introducing the retroviral vectors comprising the subject nucleic acid into packaging cell lines and of collecting the viral particles that are generated by the packaging lines are well known in the art.

Vectors used for providing nucleic acid of interest to the subject cells will typically comprise suitable promoters for driving the expression, that is, transcriptional activation, of the nucleic acid of interest. In other words, the nucleic acid of interest will be operably linked to a promoter. This may include ubiquitously acting promoters, for example, the CMV-b-actin promoter, or inducible promoters, such as promoters that are active in particular cell populations or that respond to the presence of drugs such as tetracycline. By transcriptional activation, it is intended that transcription will be increased above basal levels in the target cell by at least about 10 fold, by at least about 100 fold, more usually by at least about 1000 fold. In addition, vectors used for providing the subject nucleic acids to the cells may include genes that must later be removed, e.g. using a recombinase system such as Cre/Lox, or the cells that express them destroyed, e.g. by including genes that allow selective toxicity such as herpesvirus TK, bcl-xs, etc Agents suitable for inhibiting non-canonical Notch signaling genes in the subject methods also include polypeptides. Such polypeptides may optionally be fused to a polypeptide domain that increases solubility of the product. The domain may be linked to the polypeptide through a defined protease cleavage site, e.g. a TEV sequence, which is cleaved by TEV protease. The linker may also include one or more flexible sequences, e.g. from 1 to 10 glycine residues. In some embodiments, the cleavage of the fusion protein is performed in a buffer that maintains solubility of the product, e.g. in the presence of from 0.5 to 2 M urea, in the presence of polypeptides and/or polynucleotides that increase solubility, and the like. Domains of interest include endosomolytic domains, e.g. influenza HA domain; and other polypeptides that aid in production, e.g. IF2 domain, GST domain, GRPE domain, and the like.

If the subject polypeptide agent is to inhibit the gene product intracellularly, the polypeptide may comprise the polypeptide sequences of interest fused to a polypeptide permeant domain. A number of permeant domains are known in the art and may be used in the non-integrating polypeptides of the present invention, including peptides, peptidomimetics, and non-peptide carriers. For example, a permeant peptide may be derived from the third alpha helix of Drosophila melanogaster transcription factor Antennapaedia, referred to as penetratin. As another example, the permeant peptide comprises the HIV-1 tat basic region amino acid sequence, which may include, for example, amino acids 49-57 of naturally-occurring tat protein. Other permeant domains include poly-arginine motifs, for example, the region of amino acids 34-56 of HIV-1 rev protein, nona-arginine, octa-arginine, and the like. (See, for example, Futaki et al. (2003) Curr Protein Pept Sci. 2003 April; 4(2): 87-96; and Wender et al. (2000) Proc. Natl. Acad. Sci. U.S.A 2000 Nov. 21; 97(24):13003-8; published U.S. Patent applications 20030220334; 20030083256; 20030032593; and 20030022831, herein specifically incorporated by reference for the teachings of translocation peptides and peptoids). The nona-arginine (R9) sequence is one of the more efficient PTDs that have been characterized (Wender et al. 2000; Uemura et al. 2002).

The subject polypeptide agent may be formulated for improved stability. For example, the peptides may be PEGylated, where the polyethyleneoxy group provides for enhanced lifetime in the blood stream. The polypeptide may be fused to another polypeptide to provide for added functionality, e.g. to increase the in vivo stability. Generally such fusion partners are a stable plasma protein, which may, for example, extend the in vivo plasma half-life of the polypeptide when present as a fusion, in particular wherein such a stable plasma protein is an immunoglobulin constant domain. In most cases where the stable plasma protein is normally found in a multimeric form, e.g., immunoglobulins or lipoproteins, in which the same or different polypeptide chains are normally disulfide and/or noncovalently bound to form an assembled multichain polypeptide, the fusions herein containing the polypeptide also will be produced and employed as a multimer having substantially the same structure as the stable plasma protein precursor. These multimers will be homogeneous with respect to the polypeptide agent they comprise, or they may contain more than one polypeptide agent.

Stable plasma proteins are proteins which typically exhibit in their native environment an extended half-life in the circulation, i.e. greater than about 20 hours. Examples of suitable stable plasma proteins are immunoglobulins, albumin, lipoproteins, apolipoproteins and transferrin. The polypeptide agent typically is fused to the plasma protein, e.g. IgG at the N-terminus of the plasma protein or fragment thereof which is capable of conferring an extended half-life upon the polypeptide. Increases of greater than about 100% on the plasma half-life of the polypeptide are satisfactory. Ordinarily, the polypeptide is fused C-terminally to the N-terminus of the constant region of immunoglobulins in place of the variable region(s) thereof, however N-terminal fusions may also find use. Typically, such fusions retain at least functionally active hinge, CH2 and CH3 domains of the constant region of an immunoglobulin heavy chain, which heavy chains may include IgG1, IgG2a, IgG2b, IgG3, IgG4, IgA, IgM, IgE, and IgD, usually one or a combination of proteins in the IgG class. Fusions are also made to the C-terminus of the Fc portion of a constant domain, or immediately N-terminal to the CH1 of the heavy chain or the corresponding region of the light chain. This ordinarily is accomplished by constructing the appropriate DNA sequence and expressing it in recombinant cell culture. Alternatively, the polypeptides may be synthesized according to known methods.

The site at which the fusion is made may be selected in order to optimize the biological activity, secretion or binding characteristics of the polypeptide. The optimal site will be determined by routine experimentation.

In some embodiments the hybrid immunoglobulins are assembled as monomers, or hetero- or homo-multimers, and particularly as dimers or tetramers. Generally, these assembled immunoglobulins will have known unit structures. A basic four chain structural unit is the form in which IgG, IgD, and IgE exist. A four chain unit is repeated in the higher molecular weight immunoglobulins; IgM generally exists as a pentamer of basic four-chain units held together by disulfide bonds. IgA immunoglobulin, and occasionally IgG immunoglobulin, may also exist in a multimeric form in serum. In the case of multimers, each four chain unit may be the same or different.

The polypeptide agent for use in the subject methods may be produced from eukaryotic produced by prokaryotic cells, it may be further processed by unfolding, e.g. heat denaturation, DTT reduction, etc. and may be further refolded, using methods known in the art.

Modifications of interest that do not alter primary sequence include chemical derivatization of polypeptides, e.g., acylation, acetylation, carboxylation, amidation, etc. Also included are modifications of glycosylation, e.g. those made by modifying the glycosylation patterns of a polypeptide during its synthesis and processing or in further processing steps; e.g. by exposing the polypeptide to enzymes which affect glycosylation, such as mammalian glycosylating or deglycosylating enzymes. Also embraced are sequences that have phosphorylated amino acid residues, e.g. phosphotyrosine, phosphoserine, or phosphothreonine.

Also included in the subject invention are polypeptides that have been modified using ordinary molecular biological techniques and synthetic chemistry so as to improve their resistance to proteolytic degradation or to optimize solubility properties or to render them more suitable as a therapeutic agent. Analogs of such polypeptides include those containing residues other than naturally occurring L-amino acids, e.g. D-amino acids or non-naturally occurring synthetic amino acids. D-amino acids may be substituted for some or all of the amino acid residues.

The subject polypeptide agent may be prepared by in vitro synthesis, using conventional methods as known in the art. Various commercial synthetic apparatuses are available, for example, automated synthesizers by Applied Biosystems, Inc., Beckman, etc. By using synthesizers, naturally occurring amino acids may be substituted with unnatural amino acids. The particular sequence and the manner of preparation will be determined by convenience, economics, purity required, and the like.

If desired, various groups may be introduced into the peptide during synthesis or during expression, which allow for linking to other molecules or to a surface. Thus cysteines can be used to make thioethers, histidines for linking to a metal ion complex, carboxyl groups for forming amides or esters, amino groups for forming amides, and the like.

The subject polypeptide agent may also be isolated and purified in accordance with conventional methods of recombinant synthesis. A lysate may be prepared of the expression host and the lysate purified using HPLC, exclusion chromatography, gel electrophoresis, affinity chromatography, or other purification technique. For the most part, the compositions which are used will comprise at least 20% by weight of the desired product, more usually at least about 75% by weight, preferably at least about 95% by weight, and for therapeutic purposes, usually at least about 99.5% by weight, in relation to contaminants related to the method of preparation of the product and its purification. Usually, the percentages will be based upon total protein.

Another example of polypeptide agents suitable for inhibiting non-canonical Notch genes are antibodies. The term "antibody" or "antibody moiety" is intended to include any polypeptide chain-containing molecular structure with a specific shape that fits to and recognizes an epitope, where one or more non-covalent binding interactions stabilize the complex between the molecular structure and the epitope. The specific or selective fit of a given structure and its specific epitope is sometimes referred to as a "lock and key" fit. The archetypal antibody molecule is the immunoglobulin, and all types of immunoglobulins, IgG, IgM, IgA, IgE, IgD, etc., from all sources, e.g. human, rodent, rabbit, cow, sheep, pig, dog, other mammal, chicken, other avians, etc., are considered to be "antibodies." The term "antibody" herein is used in the broadest sense and specifically covers intact antibodies, monoclonal antibodies, polyclonal antibodies, multispecific antibodies (e.g. bispecific antibodies) formed from at least two intact antibodies, and antibody fragments, so long as they exhibit the desired biological activity. Antibodies are typically provided in the media in which the cells are cultured.

Agents may be obtained from a wide variety of sources including libraries of synthetic or natural compounds. For example, numerous means are available for random and directed synthesis of a wide variety of organic compounds, including biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

The subject agent, i.e. the agent that inhibits a non-canonical Notch gene, may be used to reduce cancer cell proliferation, e.g. Notch-associated cancer cell proliferation, in cells in vivo and in vitro. In performing the subject methods, the subject agent, i.e. the agent that inhibits the non-canonical Notch gene, is provided to cells in an effective amount. By an "effective amount" it is meant the amount of subject agent that, when provided to a cancerous cell or population of cancerous cells, e.g. cells of a cancer that is associated with active Notch, e.g. in vivo or in vitro, for a suitable period of time will evidence an alteration of the proliferation of the cancerous cell(s). For example, an effective dose of subject agent is the dose that, when administered in vivo to an individual suffering from a cancer, e.g. a Notch-associated cancer, for a suitable period of time, usually at least about one week, and may be about two weeks, or more, up to a period of about 4 weeks, 8 weeks, or longer will slow, halt or reverse tumor cell growth in the individual suffering from the cancer. It will be understood by those of skill in the art that an initial dose may be administered for such periods of time, followed by maintenance doses, which, in some cases, will be at a reduced dosage. As another example, an effective amount of subject agent is the amount that when contacted to cells in vitro for a suitable period of time, usually at least about 12 hours, about 24 hours, about 48 hours, about one week, will slow, halt, or reverse the cell proliferation in vitro. Cells may be from any species, e.g. *drosophila, c. elegans*, or vertebrate, e.g. mammal, e.g. murine, rodent, canine, feline, equine, bovine, ovine, primate, human, etc.

As discussed in greater detail below, calculating the effective amount or effective dose of subject agent to be administered is within the skill of one of ordinary skill in the art, and will be routine to those persons skilled in the art. Needless to say, the final amount to be administered will be dependent upon a variety of factors, include the route of administration, the nature of the disorder or condition that is to be treated, and factors that will differ from patient to patient. A competent clinician will be able to determine an effective amount of a therapeutic agent to administer to a patient to halt or reverse the progression the disease condition as required. Utilizing $LD_{50}$ animal data, and other information available for the agent, a clinician can determine the maximum safe dose for an individual, depending on the route of administration. For instance, an intravenously administered dose may be more than an intrathecally or topically administered dose, given the greater body of fluid into which the therapeutic composition is being administered. Similarly, compositions which are rapidly cleared from the body may be administered at higher doses, or in repeated doses, in order to maintain a therapeutic concentration. Utilizing ordinary skill, the competent clinician will be able to optimize the dosage of a particular therapeutic in the course of routine clinical trials.

In some applications, the subject agent is employed to inhibit tumor growth or metastasis in vivo. In these in vivo embodiments, the subject agent is administered directly to the individual. A subject agent may be administered by any of a number of well-known methods in the art and described below for the administration of peptides, small molecules and nucleic acids to a subject. The subject agent can be incorporated into a variety of formulations. More particularly, the subject agent of the present disclosure can be formulated into pharmaceutical compositions by combination with appropriate pharmaceutically acceptable carriers or diluents.

The amount administered varies depending upon the goal of the administration, the health and physical condition of the individual to be treated, age, the taxonomic group of individual to be treated (e.g., human, non-human primate, primate, etc.), the degree of resolution desired, the formulation of the subject agent composition, the treating clinician's assessment of the medical situation, and other relevant factors. It is expected that the amount will fall in a relatively broad range that can be determined through routine trials. For example, the amount of subject agent employed to inhibit cancer metastasis is not more than about the amount that could otherwise be irreversibly toxic to the subject (i.e., maximum tolerated dose). In other cases the amount is around or even well below the toxic threshold, but still in an immunoeffective concentration range, or even as low as threshold dose.

Individual doses are typically not less than an amount required to produce a measurable effect on the subject, and may be determined based on the pharmacokinetics and pharmacology for absorption, distribution, metabolism, and excretion ("ADME") of the subject agent and of its byproducts, and thus based on the disposition of the composition within the subject. This includes consideration of the route of administration as well as dosage amount, which can be adjusted for topical (applied directly where action is desired for mainly a local effect), enteral (applied via digestive tract for systemic or local effects when retained in part of the digestive tract), or parenteral (applied by routes other than the digestive tract for systemic or local effects) applications. For instance, administration of the subject agent may be topical or via injection, e.g. intravenous, intramuscular, or intratumoral injection or a combination thereof.

The subject agent may be administered by infusion or by local injection, e.g. by infusion at a rate of about 50 mg/h to about 400 mg/h, including about 75 mg/h to about 375 mg/h, about 100 mg/h to about 350 mg/h, about 150 mg/h to about 350 mg/h, about 200 mg/h to about 300 mg/h, about 225 mg/h to about 275 mg/h. Exemplary rates of infusion can achieve a desired therapeutic dose of, for example, about 0.5 mg/m$^2$/day to about 10 mg/m$^2$/day, including about 1 mg/m$^2$/day to about 9 mg/m$^2$/day, about 2 mg/m$^2$/day to about 8 mg/m$^2$/day, about 3 mg/m$^2$/day to about 7 mg/m$^2$/day, about 4 mg/m$^2$/day to about 6 mg/m$^2$/day, about 4.5 mg/m$^2$/day to about 5.5 mg/m$^2$/day. Administration (e.g., by infusion) can be repeated over a desired period, e.g., repeated over a period of about 1 day to about 5 days or once every several days, for example, about five days, over about 1 month, about 2 months, etc. It also can be administered prior, at the time of, or after other therapeutic interventions, such as surgical intervention to remove cancerous cells. The subject agent can also be administered as part of a combination therapy, in which at least one of an immunotherapy, a cancer chemotherapy or a radiation therapy is administered to the subject (as described in greater detail below).

Disposition of the subject agent and its corresponding biological activity within a subject is typically gauged against the fraction of aPKC iota inhibitor present at a target of interest. For example, a subject agent once administered can accumulate with a glycoconjugate or other biological target that concentrates the material in cancer cells and cancerous tissue. Thus dosing regimens in which the subject agent is administered so as to accumulate in a target of interest over time can be part of a strategy to allow for lower individual doses. This can also mean that, for example, the dose of subject agent that are cleared more slowly in vivo can be lowered relative to the effective concentration calculated from in vitro assays (e.g., effective amount in vitro approximates mM concentration, versus less than mM concentrations in vivo).

As an example, the effective amount of a dose or dosing regimen can be gauged from the IC$_{50}$ of a given subject agent for inhibiting cell proliferation. By "IC$_{50}$" is intended the concentration of a drug required for 50% inhibition in vitro. Alternatively, the effective amount can be gauged from the EC$_{50}$ of a given subject agent concentration. By "EC$_{50}$" is intended the plasma concentration required for obtaining 50% of a maximum effect in vivo. In related embodiments, dosage may also be determined based on ED$_{50}$ (effective dosage).

In general, with respect to the subject agent of the present disclosure, an effective amount is usually not more than 200× the calculated IC$_{50}$. Typically, the amount of an subject agent that is administered is less than about 200×, less than about 150×, less than about 100× and many embodiments less than about 75×, less than about 60×, 50×, 45×, 40×, 35×, 30×, 25×, 20×, 15×, 10× and even less than about 8× or 2× than the calculated IC$_{50}$. In one embodiment, the effective amount is about 1× to 50× of the calculated IC$_{50}$, and sometimes about 2× to 40×, about 3× to 30× or about 4× to 20× of the calculated IC$_{50}$. In other embodiments, the effective amount is the same as the calculated IC$_{50}$, and in certain embodiments the effective amount is an amount that is more than the calculated IC$_{50}$. An effect amount may not be more than 100× the calculated EC$_{50}$. For instance, the amount of an subject agent that is administered is less than about 100×, less than about 50×, less than about 40×, 35×, 30×, or 25× and many embodiments less than about 20×, less than about 15× and even less than about 10×, 9×, 9×, 7×, 6×, 5×, 4×, 3×, 2× or 1× than the calculated EC$_{50}$. The effective amount may be about 1× to 30× of the calculated EC$_{50}$, and sometimes about 1× to 20×, or about 1× to 10× of the calculated EC$_{50}$. The effective amount may also be the same as the calculated EC$_{50}$ or more than the calculated EC$_{50}$. The IC$_{50}$ can be calculated by inhibiting cell proliferation and/or cell migration/invasion in vitro. The procedure can be carry out by methods known in the art or as described in the examples below.

Effective amounts of dose and/or dose regimen can readily be determined empirically from assays, from safety and escalation and dose range trials, individual clinician-patient relationships, as well as in vitro and in vivo assays such as those described herein and illustrated in the Experimental section, below. For example, a concentration used for carrying out the subject method in mice ranges from about 1 mg/kg to about 25 mg/kg based on the body weight of the mice. Based on this data, an example of a concentration of the subject agent that can be employed in human may range about 0.083 mg/kg to about 2.08 mg/kg. Other dosage may be determined from experiments with animal models using methods known in the art (Reagan-Shaw et al. (2007) *The FASEB Journal* 22:659-661).

The subject agent can be incorporated into a variety of formulations. More particularly, the subject agent may be formulated into pharmaceutical compositions by combination with appropriate pharmaceutically acceptable carriers or diluents. Pharmaceutical preparations are compositions that include one or more subject agent present in a pharmaceutically acceptable vehicle. "Pharmaceutically acceptable vehicles" may be vehicles approved by a regulatory agency of the Federal or a state government or listed in the U.S. Pharmacopeia or other generally recognized pharmacopeia for use in mammals, such as humans. The term "vehicle" refers to a diluent, adjuvant, excipient, or carrier with which a compound of the invention is formulated for administration to a mammal. Such pharmaceutical vehicles can be lipids, e.g. liposomes, e.g. liposome dendrimers; liquids, such as water and oils, including those of petroleum, animal, vegetable or synthetic origin, such as peanut oil, soybean oil, mineral oil, sesame oil and the like, saline; gum acacia, gelatin, starch paste, talc, keratin, colloidal silica, urea, and the like. In addition, auxiliary, stabilizing, thickening, lubricating and coloring agents may be used.

Pharmaceutical compositions may be formulated into preparations in solid, semi-solid, liquid or gaseous forms, such as tablets, capsules, powders, granules, ointments, solutions, suppositories, injections, inhalants, gels, microspheres, and aerosols. As such, administration of the subject agent can be achieved in various ways, including transdermal, intradermal, oral, buccal, rectal, parenteral, intraperitoneal, intradermal, intracheal, etc., administration. The active agent may be systemic after administration or may be localized by the use of regional administration, intramural administration, or use of an implant that acts to retain the active dose at the site of implantation. The active agent may be formulated for immediate activity or it may be formulated for sustained release.

For some conditions, particularly central nervous system conditions, it may be necessary to formulate agents to cross the blood-brain barrier (BBB). One strategy for drug delivery through the blood-brain barrier (BBB) entails disruption of the BBB, either by osmotic means such as mannitol or leukotrienes, or biochemically by the use of vasoactive substances such as bradykinin. The potential for using BBB opening to target specific agents to brain tumors is also an option. A BBB disrupting agent can be co-administered with the therapeutic compositions of the invention when the compositions are administered by intravascular injection. Other strategies to go through the BBB may entail the use of endogenous transport systems, including Caveolin-1 mediated transcytosis, carrier-mediated transporters such as glucose and amino acid carriers, receptor-mediated transcytosis for insulin or transferrin, and active efflux transporters such as p-glycoprotein. Active transport moieties may also be conjugated to the therapeutic compounds for use in the invention to facilitate transport across the endothelial wall of the blood vessel.

Alternatively, drug delivery of subject agent behind the BBB may be by local delivery, for example by intrathecal delivery, e.g. through an Ommaya reservoir (see e.g. U.S. Pat. Nos. 5,222,982 and 5,385,582, incorporated herein by reference); by bolus injection, e.g. by a syringe, e.g. intravitreally or intracranially; by continuous infusion, e.g. by cannulation, e.g. with convection (see e.g. US application Ser. No. 20070254842, incorporated here by reference); or by implanting a device upon which the agent has been reversably affixed (see e.g. US application Ser. Nos. 20080081064 and 20090196903, incorporated herein by reference).

For inclusion in a medicament, the subject agent may be obtained from a suitable commercial source. As a general proposition, the total pharmaceutically effective amount of the subject agent administered parenterally per dose will be in a range that can be measured by a dose response curve.

Non-canonical Notch signaling-based therapies, i.e. preparations of subject agent that inhibits a non-canonical Notch signaling protein, to be used for therapeutic administration, may be sterile. Sterility is readily accomplished by filtration through sterile filtration membranes (e.g., 0.2 µm membranes). Therapeutic compositions generally are placed into a container having a sterile access port, for example, an intravenous solution bag or vial having a stopper pierceable by a hypodermic injection needle. The subject agent-based therapies may be stored in unit or multi-dose containers, for example, sealed ampules or vials, as an aqueous solution or as a lyophilized formulation for reconstitution. As an example of a lyophilized formulation, 10-mL vials are filled with 5 ml of sterile-filtered 1% (w/v) aqueous solution of compound, and the resulting mixture is lyophilized. The infusion solution is prepared by reconstituting the lyophilized compound using bacteriostatic Water-for-Injection. Alternatively, the subject agent may be formulated into lotions for topical administration.

Pharmaceutical compositions can include, depending on the formulation desired, pharmaceutically-acceptable, non-toxic carriers of diluents, which are defined as vehicles commonly used to formulate pharmaceutical compositions for animal or human administration. The diluent is selected so as not to affect the biological activity of the combination. Examples of such diluents are distilled water, buffered water, physiological saline, PBS, Ringer's solution, dextrose solution, and Hank's solution. In addition, the pharmaceutical composition or formulation can include other carriers, adjuvants, or non-toxic, nontherapeutic, nonimmunogenic stabilizers, excipients and the like. The compositions can also include additional substances to approximate physiological conditions, such as pH adjusting and buffering agents, toxicity adjusting agents, wetting agents and detergents. The composition can also include any of a variety of stabilizing agents, such as an antioxidant for example. When the pharmaceutical composition includes a polypeptide, the polypeptide can be complexed with various well-known compounds that enhance the in vivo stability of the polypeptide, or otherwise enhance its pharmacological properties (e.g., increase the half-life of the polypeptide, reduce its toxicity, enhance solubility or uptake). Examples of such modifications or complexing agents include sulfate, gluconate, citrate and phosphate. The nucleic acids or polypeptides of a composition can also be complexed with molecules that enhance their in vivo attributes. Such molecules include, for example, carbohydrates, polyamines, amino acids, other peptides, ions (e.g., sodium, potassium, calcium, magnesium, manganese), and lipids.

Further guidance regarding formulations that are suitable for various types of administration can be found in Remington's Pharmaceutical Sciences, Mace Publishing Company, Philadelphia, Pa., 17th ed. (1985). For a brief review of methods for drug delivery, see, Langer, Science 249: 1527-1533 (1990).

The pharmaceutical compositions can be administered for prophylactic and/or therapeutic treatments. Toxicity and therapeutic efficacy of the active ingredient can be determined according to standard pharmaceutical procedures in cell cultures and/or experimental animals, including, for example, determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Therapies that exhibit large therapeutic indices are preferred.

The data obtained from cell culture and/or animal studies can be used in formulating a range of dosages for humans. The dosage of the active ingredient typically lines within a range of circulating concentrations that include the ED50 with low toxicity. The dosage can vary within this range depending upon the dosage form employed and the route of administration utilized.

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile. To the extent that a given compound must be synthesized prior to use, the resulting product is typically substantially free of any potentially toxic agents, particularly any endotoxins, which may be present during the synthesis or purification process. Compositions for parental administration are also sterile, substantially isotonic and made under GMP conditions.

The subject agent may be provided in addition to other agents. For example, in methods of treating cancer, e.g. a cancer associated with active Notch, a subject agent may be coadministered with other known cancer therapies, or with an agent that inhibits canonical Notch signaling, e.g. an inhibitor of γ secretase, an inhibitor of a CSL transcription factor, an inhibitor of a mastermind transcription co-factor, etc.

In other instances, the subject agent is contacted to cells in vitro. For example, the subject agents may be contacted to cells in vitro as a control agent in screening methods to identify candidate agents for use in treating cancer, or in screens to identify candidate agents that work synergistically to treat a cancer, e.g. a Notch-associated cancer. As another example, the subject agent may be contacted to cells in vitro to determine if the individual's cancer will be responsive to the subject agent. In these and other in vitro methods, cells may be from established cell lines or they may be primary cells, where "primary cells", "primary cell lines", and "primary cultures" are used interchangeably herein to refer to cells and cells cultures that have been derived from a subject and allowed to grow in vitro for a limited number of passages, i.e. splittings, of the culture. For example, primary cultures are cultures that may have been passaged 0 times, 1 time, 2 times, 4 times, 5 times, 10 times, or 15 times, but not enough times go through the crisis stage. Typically, the primary cell lines of the present invention are maintained for fewer than 10 passages in vitro.

If the cells are primary cells, they may be harvest from an individual by any convenient method. For example, cells, e.g. blood cells, e.g. leukocytes, e.g. cancerous leukocytes, may be harvested by apheresis, leukocytapheresis, density gradient separation, etc. As another example, cells, e.g. skin, muscle, bone marrow, spleen, liver, pancreas, lung, intestine, stomach, nervous system tissue, etc. may be harvested by biopsy. An appropriate solution may be used for dispersion or suspension of the harvested cells. Such solution will generally be a balanced salt solution, e.g. normal saline, PBS, Hank's balanced salt solution, etc., conveniently supplemented with fetal calf serum or other naturally occurring factors, in conjunction with an acceptable buffer at low concentration, generally from 5-25 mM. Convenient buffers include HEPES, phosphate buffers, lactate buffers, etc. The cells may be used immediately, or they may be stored, frozen, for long periods of time, being thawed and capable of being reused. In such cases, the cells will usually be frozen in 10% DMSO, 50% serum, 40% buffered medium, or some other such solution as is commonly used in the art to preserve cells at such freezing temperatures, and thawed in a manner as commonly known in the art for thawing frozen cultured cells.

To modulate cancer cell proliferation in vitro, the subject agent is provided to the cells for about 30 minutes to about 24 hours, e.g., 1 hour, 1.5 hours, 2 hours, 2.5 hours, 3 hours, 3.5 hours 4 hours, 5 hours, 6 hours, 7 hours, 8 hours, 12 hours, 16 hours, 18 hours, 20 hours, or any other period from about 30 minutes to about 24 hours, which may be repeated with a frequency of about every day to about every 4 days, e.g., every 1.5 days, every 2 days, every 3 days, or any other frequency from about every day to about every four days. The subject agent may be provided to the subject cells one or more times, e.g. one time, twice, three times, or more than three times, and the cells allowed to incubate with the agent for some amount of time following each contacting event e.g. 16-24 hours, after which time the media is replaced with fresh media and the cells are cultured further.

Contacting the cells with the subject agent may occur in any culture media and under any culture conditions that promote the survival of the cells. For example, cells may be suspended in any appropriate nutrient medium that is convenient, such as Iscove's modified DMEM or RPMI 1640, supplemented with fetal calf serum or heat inactivated goat serum (about 5-10%), L-glutamine, a thiol, particularly 2-mercaptoethanol, and antibiotics, e.g. penicillin and streptomycin. The culture may contain growth factors to which the cells are responsive. Growth factors, as defined herein, are molecules capable of promoting survival, growth and/or differentiation of cells, either in culture or in the intact tissue, through specific effects on a transmembrane receptor. Growth factors include polypeptides and non-polypeptide factors.

As discussed above, the subject disclosure also envisions the application of the discoveries herein of the relevance of non-canonical Notch signaling to cancer to screening candidate agents to identify those with the ability to treat a Notch-associated cancer. In one embodiment, a method of identifying a candidate agent having the ability to treat a Notch-associated cancer is provided, the method comprising: contacting a cancer cell comprising a mitochondria-targeted construct comprising a GFP expression cassette with the candidate agent, comparing mitochondrial morphology in the cell to the mitochondrial morphology in a cancer cell comprising a mitochondria-targeted construct comprising a GFP expression cassette that has not been contacted with the candidate agent, and identifying a candidate agent having the ability to treat a cancer based on the comparison, wherein aggregated mitochondrial morphology in the cancer cell contacting with candidate agent indicates that the candidate agent will have the ability to treat a Notch-associated cancer.

In another embodiment, a method of identifying a candidate agent having the ability to treat a Notch-associated cancer is provided, the method comprising contacting a cancer cell comprising active Notch with the candidate agent, comparing mitochondrial respiration in the cancer cell to the mitochondrial respiration in a cancer cell comprising active Notch that has not been contacted with the candidate agent, and identifying a candidate agent having the ability to treat a Notch-associated cancer based on the comparison, wherein impaired mitochondrial respiration in the cancer cell contacted with the agent indicates that the candidate agent will have the ability to treat a Notch-associated cancer.

In another embodiment, a method of identifying a candidate agent having the ability to treat a Notch-associated cancer is provided, the method comprising contacting a cancer cell comprising active Notch with the candidate agent, comparing AKT phosphorylation in the cancer cell to AKT phosphorylation in a cancer cell comprising active Notch that has not been contacted with the candidate agent, and identifying a candidate agent having the ability to treat a Notch-associated cancer based on the comparison, wherein decreased AKT phosphorylation in the cancer cell contacted with the agent indicates that the candidate agent will have the ability to treat a cancer associated with constitutive Notch activity.

Methods for performing these screens will be readily understood by the ordinarily skilled artisan in view of the teachings in the art and the working examples herein.

Reagents, Devices and Kits

Also provided are reagents, devices and kits thereof for practicing one or more of the above-described methods. The subject reagents, devices and kits thereof may vary greatly. Reagents and kits of interest include those mentioned above with respect to the methods of treating a cancer, and may include, for example, one or more reagents for determining if an individual has a Notch-associated cancer, and a pharmaceutical composition comprising an agent that inhibits a non-canonical Notch signaling gene.

In addition to the above components, the subject kits will further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

General methods in molecular and cellular biochemistry can be found in such standard textbooks as Molecular Cloning: A Laboratory Manual, 3rd Ed. (Sambrook et al., HaRBor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998), the disclosures of which are incorporated herein by reference. Reagents, cloning vectors, and kits for genetic manipulation referred to in this disclosure are available from commercial vendors such as BioRad, Stratagene, Invitrogen, Sigma-Aldrich, and ClonTech.

Example 1

Maintaining a delicate balance between self-renewal and differentiation is a hallmark of all stem cells (Doe, 2008; Morrison and Kimble, 2006; Zhong and Chia, 2008). Impairments of such balance can lead to lineage depletion or tumorigenesis. The self-renewal vs. differentiation decision of mammalian NSCs and Drosophila neuroblasts (NBs), an excellent model for neural stem cell (NSC) biology (Doe, 2008; Knoblich, 2010; Sousa-Nunes et al., 2010), requires Notch (N) signaling (Andersson et al., 2011; Artavanis-Tsakonas and Muskavitch, 2010; Wang et al., 2006). In the type II NB lineages of the Drosophila larval central brain, which contain transit-amplifying intermediate progenitors (IPs) and are similar to mammalian NSCs in lineage hierarchy (FIG. 1A), inhibition of N signaling leads to NB loss, whereas N activation causes the dedifferentiation of IPs into ectopic NBs (Bowman et al., 2008; Song and Lu, 2011; Weng et al., 2010) reminiscent of the cell of origin of brain tumors in mammals (Dirks, 2010; Liu and Zong, 2012). The mechanism by which N signaling maintains NB lineage homeostasis is not well defined. N can signal through Suppressor of Hairless [Su(H)] to transcriptionally regulates its target gene Myc, whose regulation of cell growth is critical for the maintenance of NSCs and cancer stem cell (CSC)-like cells in Drosophila. However, overexpression of Myc alone is insufficient to mimic the effect of N in promoting ectopic NSC formation (Song and Lu, 2011), suggesting the involvement of other pathway(s).

The experiments below demonstrate that a novel non-canonical N signaling pathway is involved in N-directed stem cell regulation. In this pathway, N interacts with PTEN-induced kinase 1 (PINK1) to influence mitochondrial function, activating mechanistic target of rapamycin complex 2 (mTORC2)/AKT signaling and enhancing NB growth and proliferation. Importantly, attenuating the non-canonical N signaling pathway preferentially impaired the maintenance of Drosophila and human brain cancer stem cell (CSC)-like cells. Canonical N signaling, which promotes nucleolar growth, acted together with the newly identified non-canonical N signaling pathway to maintain normal NBs. Moreover, co-activation of canonical and non-canonical N signaling was sufficient to induce the dedifferentiation of IPs into ectopic NBs, recapitulating the effect of N activation. Our results identify a non-canonical N signaling pathway preferentially required by cancer stem cell-like cells, emphasize the under-appreciated importance of mitochondria in N and stem cell biology, and have important implications for cancer and other diseases caused by aberrant N signaling.

Materials and Methods

Fly genetics. Fly culture and crosses were performed according to standard procedures and were raised at indicated temperatures. Drosophila stocks used in this study are: dPINK1$^{B9}$(JK Chung); Drp1$^2$ (H. Bellen); N$^{55e11}$; NiGFP/+ (F. Schweisguth); 1407-Gal4 (L. Luo); PntP1-Gal4 (Y N. Jan); Erm-Gal4 (C. Y. Lee and G. Rubin); Mhc-Gal4 (T. Littleton); UAS-N–V5 (M. Fortini); dPINK1, dPINK1-RNAi, and Parkin transgenes were described previously (Yang et al., 2006). The other transgenes are: dMyc (F. Demontis and B. Edgar); rictor; dAKT-S505D (S. Cohen); mitoGFP (W. Saxton); Marf-RNAi (M. Guo); white-RNAi (D. Smith); NECN (deletion of the entire intracellular domain of N), NΔcdc10 (deletion of the intracellular domain of N comprising the Su(H) interacting region; E. Giniger); ND75-RNAi (2286-R-3) (National Institute of Genetics Fly Stock Center, Japan); Complex III-RNAi (v33015); dMyc-RNAi (v106066), dMyc-RNAi-2 (v17487), N-RNAi (v1112, v27229), Dicer2 (v60008; VDRC); Mam-WT (B27743), Su(H)myc (B5814), Mam-DN (dominant negative, B26672), Trc-DN (B32086), Su(H)-RNAi (B28900), rictor-RNAi (B31388), rictor-RNAi (B31527), dAKT-RNAi (B33615), dPGC1-RNAi (B33914), Notch's (B2533), Shaggy-DN (B5255), TCF-N (B4784), Smoothened-RNAi (B27037), and all other stocks were obtained from Bloomington Drosophila Stock Center (USA). To enhance the efficiency of N knockdown, Dicer2 was coexpressed with N-RNAi (Song and Lu, 2011).

MARCM and flip-out clonal analysis. To generate NB MARCM clones and overexpression clones, 24 h after larval hatching (ALH) larvae were heat-shocked at 37° C. for 90 min and further aged for 72 hrs at 25° C. before dissection. MARCM analyses were performed essentially as described (Song and Lu, 2011). For making overexpression clones, w, hsFLP; Actin 5c>CD2>Gal4, UAS-GFP-NLS was crossed with the indicated UAS lines and 24 h ALH larvae were heat-shocked at 37° C. for 90 min and further aged for 72 hrs at 25° C. before dissection.

Abnormal Wing Posture.

Abnormal wing posture was analyzed as described (Yang et al., 2006). Briefly, the number of flies with abnormal wing posture (either held-up or drooped) was scored after male flies of the indicated genotypes were aged for 14 days at 29° C. For each experiment, at least 60 flies in three separate vials were scored and the percentage of flies with abnormal wing posture was presented for each genotype.

ATP measurement. The ATP level in Drosophila thoracic muscle was measured essentially as previously described (Wu et al., 2013), using a luciferase-based bioluminescence assay (ATP Bioluminescence Assay Kit HS II, Roche Applied Science).

Statistical analysis. Statistical significance of all data were evaluated by unpaired Student's t-tests Pharmacological treatment of larvae. Mdivi-1 (Enzo Life Science) dissolved in 0.5% DMSO was mixed in instant Drosophila media at 5 µM final concentration. 0.5% DMSO alone was used as vehicle control. Embryos were collected on Mdivi-1 containing food or control food for 6 hrs at 25° C. and allowed to develop further to 120 hr ALH before larval brain dissection and immunostaining.

Mammalian GBM and NSC methods. SU-GBM002 line was generated from freshly resected human GBM sample acquired under IRB 18672 approved protocol. Tissue sample was dissociated by collagenase IV (1 mg/ml), and treated with ACK/RBC lysis buffer (0.15 M $NH_4Cl$, 1.0 mM $KHCO_3$ and 0.1 mM $Na_2$-EDTA), and plated at sub clonal density for neurosphere formation in Tumor Stem media (TSM) consisting of Neurobasal(-A) (Invitrogen), B27(-A) (Invitrogen), human-bFGF (20 ng/ml) (Shenandoah Biotech), human-EGF (20 ng/ml) (Shenandoah Biotech), and heparin (10 ng/ml). Fetal forebrain tissue from gestational week 22 was acquired from approved vendor (Stem Express), dissociated using the above protocol, and plated in TSM media with the addition of recombinant human LIF (10 ng/ml) (Millipore). Neurospheres were observed after 2 weeks in culture and maintained in serum free defined media. To test for the effect of Mdivi-1, Ku-0063794, and rotenone on GBM CSCs as compared to fetal brain derived NSCs, 100 cells/well were plated in a 96 well plate and treated with Mdivi-1 (5 ρM), Ku-0063794 (5 nM), rotenone (10 nM) or DMSO vehicle control. Number of spheres regenerated was counted. For secondary sphere formation, spheres were dissociated from the inhibitor treated cultures, replated without inhibitors at 100 cells/well in a 96-well plate, and counted for the number of spheres per well.

To test the effect of PINK1 inhibition on cell proliferation of human NSC and GBM, we used lentiviral vectors expressing PINK1 shRNA (TRCN7099: 5'-TAGAT-GAAGCACATTTGC GGC-3' (SEQ ID NO:1) and TRCN7101: 5'-TATCAGATACTCCTCCAGCCG-3' (SEQ ID NO:2); Open Biosystems). Preparation of lentivirus in HEK293T cells was performed as described (Salmon and Trono, 2007) and concentrated with PEG-it virus precipitation solution (System Biosciences). NSC and GBM samples were dissociated into single cell suspensions prior to plating into 96-well chambers ($5.0 \times 10^5$ cells/well) in a 1:10 dilution of serum-free growth media to lentivirus diluted in DMEM in 25 mM HEPES (Corning). Cells were subsequently transferred to 6-well plates for transfection and were incubated at 37° C., 5% $CO_2$. To measure the impact of PINK1 shRNA knockdown on cell proliferation, dissociated NSC and GBM cells were plated into 96 well plates (10,000 cells/well), transfected with 1:10 dilution of virus for 0, 24, 48, and 96 hours, and assayed with WST-1 reagent according to manufacturer's instructions (Roche).

Immunohistochemistry. For larval brain immunostaining, larvae were dissected in Schneider's medium (Invitrogen) and fixed with 4% formaldehyde in PEM buffer (100 mM PIPES at pH 6.9, 1 mM EGTA, 1 mM $MgCl_2$) for 23 min at room temperature. Immunohistochemistry of TH and mito-GFP in Drosophila brain was performed as described (Wu et al., 2013). The primary antibodies used were: chicken anti-GFP (1:2000; Abcam), mouse anti-Pros (1:200) and mouse anti-NICD (1:100; Developmental Studies Hybridoma Bank [DSHB]), guinea pig anti-Dpn (1:1000; J. Skeath), rabbit anti-Dpn (1:1000; Y N Jan), guinea pig anti-Ase (1:400; Y N. Jan), mouse anti-fibrillarin (1:20; Abcam), rabbit anti-pS505-dAkt (1:200; Cell Signaling Technology), rabbit anti-TH (1:500), rabbit anti-Tom20 (1:200, Santa Cruz), goat anti-GAPDH (1:200; Abcam). Corresponding secondary antibodies were from Molecular Probe (all at 1:200 dilution). For thoracic muscle mitochondrial morphology analysis, mito-GFP was expressed in thoracic muscle using the Mhc-Gal4 driver and indirect flight muscles were dissected in PBS and examined under fluorescence confocal microscope. For human GBM immunostaining, the samples were washed with 1×PBS and fixed with 4% formaldehyde in 1×PBS for 15 min at room temperature. After washing, GBM cells were permeablilized with 1×PBS containing 0.25% Triton X-100 for 10 min at 4° C. Fixatives were subsequently blocked with 5% normal goat serum in 1×PBS. The primary antibodies used were: MitoTracker DeepRed FM (Invitrogen); mouse anti-PINK1 (1:5; NeuroMab); rat anti-hNotch1 (1:200; DSBH, bTAN-20).

Co-Immunoprecipitation and Western blot analysis. Approximately 25 adult fly thoraces were collected and homogenized in HBS buffer (210 mM Mannitol, 70 mM Sucrose, 5 mM HEPES pH 7.4, 1 mM EGTA) containing protease inhibitor (Sigma). The lysate was centrifuged at 1,300 g for 10 min, and the supernatant was collected and centrifuged again at 13,000 g for 15 min. For co-IP, the cytosolic and the mitochondrial fractions were incubated with anti-GFP conjugated protein G-agarose beads (Upstate) at 4° C. for 2 hours. Beads were washed 3× with PBS for 5 min each. Proteins were eluted and analyzed by WB as described (Wu et al., 2013). For co-IP assays using human NSC and GBM cells, soluble extracts of isolated mitochondrial fractions were incubated with a mixture of anti-human PINK1 (Abcam) and protein G-agarose beads (Upstate). The primary antibodies used were: pS505-dAKT and AKT (Cell Signaling Technology), Actin (Millipore), NICD (DSHB), NDUFS3 (MitoScience), complex IV subunit I (MitoScience), Drp-1 (L. Pallanck), Calnexin (Novus), PDE1 (Mito-Science), Tom20 (Santa Cruz), KDEL (Enzo Life Science), Rab5 (Abcam), Rab7 (Abcam), rat anti-hNotch1 (1:200; DSBH). Rabbit anti-dPINK1 was generated as described (Yang et al., 2006).

Blue native gel analysis. Blue native gel electrophoresis reagents were purchased from Invitrogen and electrophoresis analysis was performed based on the manufacture's recommended protocol. Ten micrograms of mitochondrial protein of each genotype was loaded onto a 3-12% native gel. Electrophoresis was carried out in a buffer of 50 mM Bis, 50 mM Tricine at pH 6.8, and 0.002% of Coomassie Brilliant Blue G250.

TEM analysis. Samples (fly thoraxes) were dissected and fixed in the fixation buffer (2% glutaraldehyde, 4% poly-formaldehyde, 0.6% picric acid in 0.1 M sodium cacodylate buffer, pH 7.4) for 30 mins at room temperature. Samples were further sectioned and prepared for EM analysis by the Cell Sciences Imaging Facility of Stanford University. Images were acquired on a JEOL JEM-1400 Transmission electron microscopy.

JC-1 staining. Indirect fight muscles were dissected and incubated in *Drosophila* S2 cell culture medium supplemented with 10% fetal bovine serum and with final JC-1 dye concentration at 5 µM. After 30 mins at 37° C., samples were washed for 2 times with S2 cell culture medium and 2 times with warmed PBS buffer. For image acquisition, samples were illuminated at 488 nm excitation and emissions between 515/545 nm and 575/625 nm were collected.

Mitochondria purification. Intact mitochondria from fly heads, fly thoraces and cultured cells were purified at described previously (Wu et al., 2013). The samples were homogenized using a Dounce homogenizer. The fraction between the 22% and 50% Percoll layers containing intact mitochondria was carefully transferred into a new reaction tube, mixed with 1 volume of HBS buffer, and centrifuged at 16,000 g for 20 minutes at 4° C. The pellet was subsequently used for WB and other biochemical analyses.

Results

To test whether canonical N signaling is sufficient to account for the full effect of N on NB lineage homeostasis, we used the NB-specific 1407-Gal4, type II NB-specific Pnt-Gal4, or IP-specific Erm-Gal4 drivers to overexpress Su(H) and mastermind (Mam), key genes in the canonical N pathway, and Myc, a transcriptional target of Su(H) (Song and Lu, 2011). Compared to the controls, there was no significant change in the number of central brain NBs after these genetic manipulations (FIG. 1B,1C). Since overexpression of Su(H) or Mam was sufficient to activate canonical N signaling as indicated by upregulation of E(spl) expression (FIG. 5A), these results suggest that activation of canonical N signaling under these conditions is insufficient, and that additional pathway(s) is needed for the induction of ectopic NBs by N gain-of-function (GOF) as observed previously (Song and Lu, 2011).

We next searched for other signaling event(s) that may act together with the canonical N signaling pathway to mediate the effect of N. We found that in N GOF condition there was significant increase of p-AKT(S505) level, as measured by immunostaining and western blot (WB) analyses (FIG. 1D,1E). Since mTORC2 is the primary kinase responsible for AKT(S505) phosphorylation (Hietakangas and Cohen, 2007; Sarbassov et al., 2005), this result indicated that mTORC2 is activated in N GOF condition. Conversely, mTORC2 is inhibited in N LOF condition (FIG. 5B). No obvious change of p-AKT level was observed when Wingless or Hh signaling was altered (FIG. 6), indicating specificity of the p-AKT response to N signaling. To assess the functional significance of mTORC2 activation, we inhibited Rictor (Hietakangas and Cohen, 2007), a key component of mTORC2. Knockdown of rictor but not the control white (W) gene significantly attenuated ectopic NB induction by N (FIG. 1F,1G, 7A). These data support that activation of mTORC2 contributes significantly to N-induced NB overproliferation.

We next asked which mTORC2 effector is critically involved in NSC regulation by non-canonical N signaling. Intriguingly, in contrast to postmitotic neurons in which Tricornered (Trc), but not AKT, acts as a key effector of mTORC2 to promote neuronal maintenance (Wu et al., 2013), NBs use AKT as the key mTORC2 effector for homeostasis control, since inhibiting AKT, but not Trc, prevented N GOF-induced ectopic NB formation (FIG. 1F,1G), and a phospho-mimetic, constitutively active AKT (AKT-S505D) rescued the mTORC2 LOF effect on NSC homeostasis (FIG. 1F,1G). These results support a critical role of the mTORC2/AKT axis in N-directed NSC homeostasis. Since canonical N signaling had no obvious effect on p-AKT(S505) level (FIG. 5C, 5D), mTORC2 activation appears to be a specific effect of non-canonical N signaling.

Figure 2:
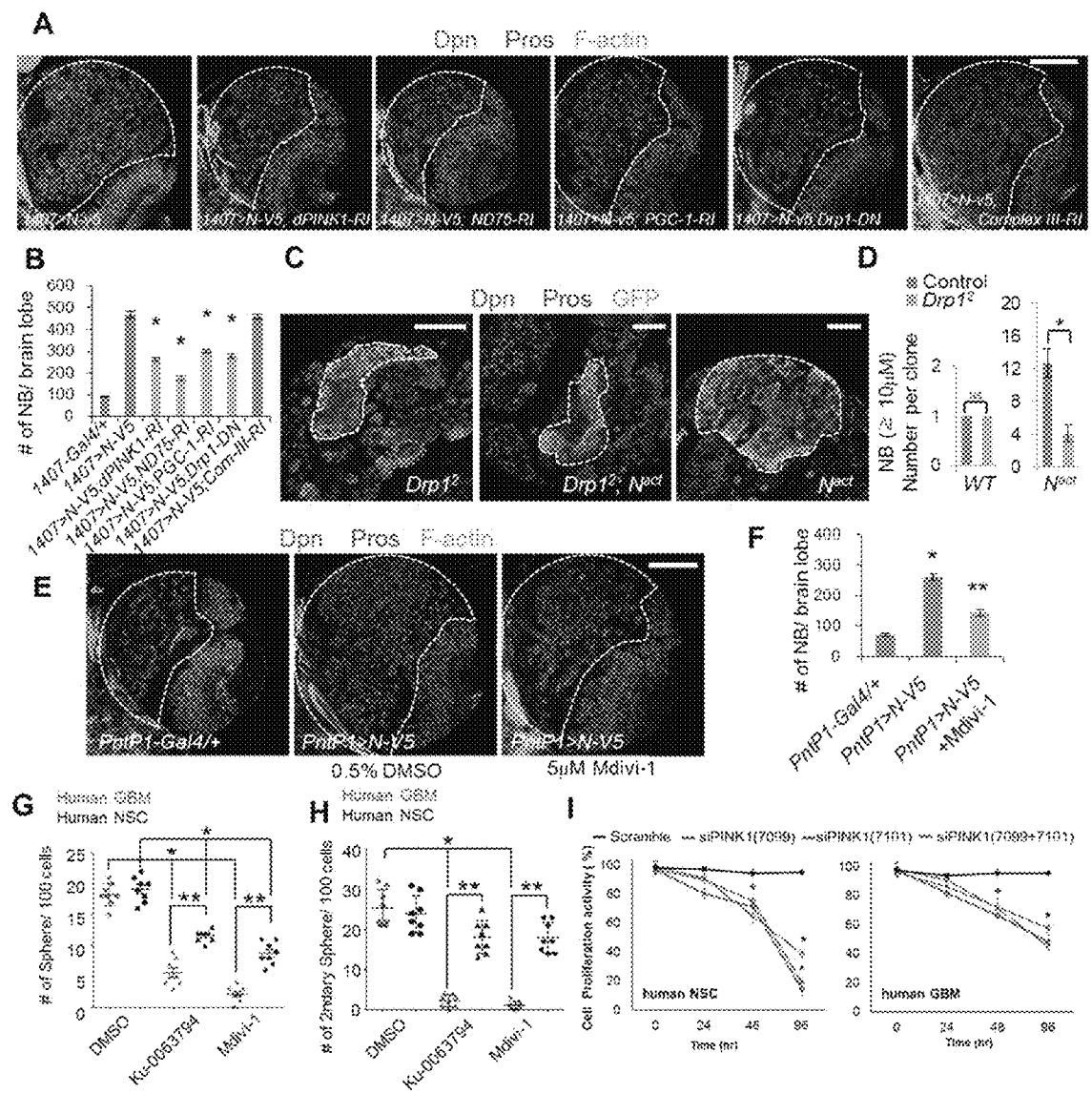
FIG. 2. Involvement of PINK1 and other mitochondrial-related genes in N-induced NB overproliferation. (A) N-induced NB expansion is blocked by inhibiting genes involved in mitochondrial regulation. Larval brains at 120 h ALH were immunostained. (B) Quantification of data from A. *, p<0.0001 versus 1407>N–V5/+; n=10. Complex-III RNAi serves as specificity control. (C) Clonal analysis of NBs in Drp1 mutant (Drp1$^2$), Drp1$^2$; N$^{act}$, and N$^{act}$ backgrounds. MARCM clones are marked with GFP and outlined with white dashed lines. (D) Quantification of data from C. NS, non-significant; *, p<0.001; n=5. (E) N-induced NB expansion is attenuated by Mdivi-1 treatment. (F) Quantification of data from E. *, p<0.001 vs. PntP1-Gal4/+; **, p<0.005 vs. PntP1>N–V5; n=5. (G, H) Primary (G) and secondary (H) neurosphere-forming activity of human GBM CSCs and normal fetal NSCs after chemical inhibition of Drp1 (Mdivi-1) or mTORC2 (Ku-0063794). *, p<0.0001 vs. DMSO control; **, p<0.001 human NSC vs. human GBM. (I) Effects of lentiviral delivery of PINK1 shRNA, either singularly or with two shRNAs combined, on the proliferation of human NSC and GBM cells. *, p<0.001 vs. scrambled shRNA control in Student's t-test. Scale bars, 100 µm (A, E); 20 µm (C).

We next sought to elucidate the signaling mechanism of the non-canonical N pathway that leads to mTORC2 activation. In flies and mammals, TOR kinase forms at least two complexes, mTORC1 and mTORC2. Compared to mTORC1, little is known about how mTORC2 is regulated by upstream signals (Zoncu et al., 2011), and its function in NSCs. Recent studies suggest that the functional state of mitochondria maintained by PINK1, a gene associated with Parkinson's disease (PD) and cancer (Devine et al., 2011), critically regulates mTORC2 activity and influences mitochondrial dynamics and function (Wu et al., 2013). Interestingly, dPINK1 null mutants exhibited defects in NB maintenance (FIG. 8A, 8B). Furthermore, partial inhibition of PINK1 by RNAi could block the activation of mTORC2 and the formation of ectopic NBs induced by N GOF (FIG. 1E, 2A), although normal NBs were largely unaffected. RNAi-mediated inhibition of several other genes implicated in mitochondrial regulation, including ND-75 [respiratory chain complex-I (RCC-I) 75 kD subunit], PGC-1α (biogenesis), and Drp1 (fission), also rescued the ectopic NB formation induced by N GOF, without affecting normal NBs. In comparison, RNAi of W or an RCC-III component failed to rescue N GOF effect (FIG. 2A, 2B, FIG. 7A). Genetic manipulations of PINK1 and the mitochondria-related genes also rescued the larval lethality induced by N GOF (FIG. 8C). Treatment of N-GOF larvae with a small molecule inhibitor of Drp1 (Cassidy-Stone et al., 2008) induced mitochondrial fusion/aggregation (FIG. 9A) and partially prevented ectopic NB formation and brain tumor formation (FIG. 2E, 2F). The role of mitochondrial fission was further evaluated by analyzing drp1 null mutant NB clones, in which normal NBs were maintained but activated N-induced ectopic NBs were largely abolished (FIG. 2C, 2D).

To test the relevance of these findings to humans, we turned to glioblastoma multiforme (GBM), where altered N and mTOR signaling have been implicated (Cloughesy et al., 2013; Dirks, 2010). Using patient-derived GBM lines that exhibited elevated N and PINK1 expression (FIG. 3K), N and mTORC2 signaling (FIG. 10A), and RCC assembly (FIG. 10B), we pharmacologically inhibited Drp1 (Cassidy-Stone et al., 2008), mTORC2 (Garcia-Martinez et al., 2009), or RCC-I. We found that growth and self-renewal of GBM CSCs were preferentially impaired by these treatments (FIG. 2G,2H, 9B,9C), supporting a critical and conserved role of the newly identified non-canonical N signaling pathway in preserving CSCs. We also examined the effect of genetically inhibiting PINK1 in human NSC and GBM cell cultures. Consistent with PINK1 function being required in both normal NSCs and CSCs, shRNA-mediated knockdown of PINK1 inhibited cell proliferation in normal NSC and GBM CSC cultures (FIG. 2I).

Figure 3:
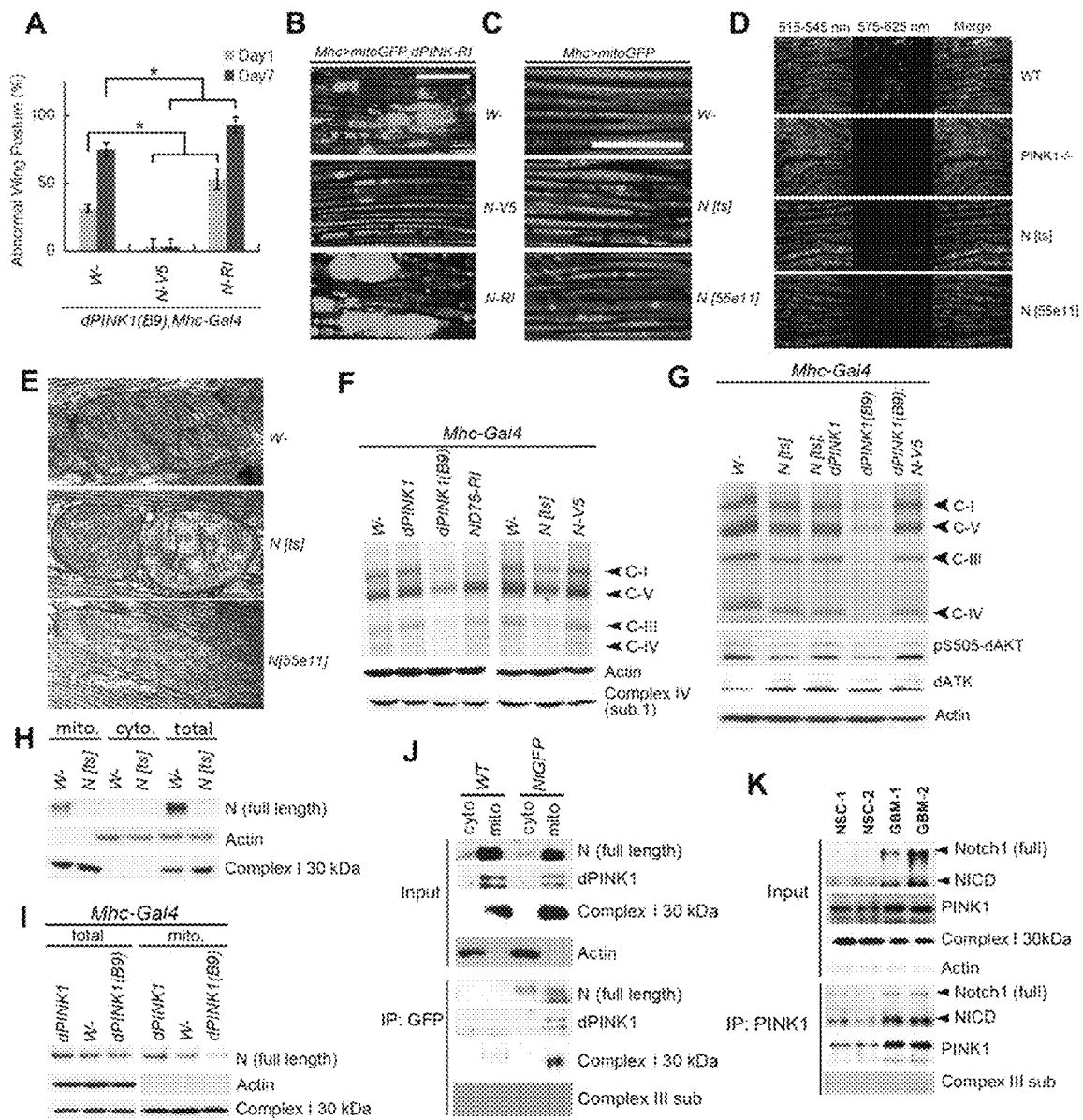
FIG. 3. Genetic and biochemical interactions between N and PINK1. (A, B) Effects of N overexpression (OE) or N RNAi on PINK1 LOF-induced abnormal wing posture (A) and aggregation of muscle mitochondria (B). *, p<0.0001 vs. w control in Student's t-test. (C) Effects of N LOF on muscle mitochondrial morphology monitored with mito-GFP. The uneven and enhanced mito-GFP signals suggest mitochondrial aggregation. (D) Effects of N mutations on mitochondrial membrane potential (indicated by JC-1 signal at 575-625 nm). PINK1 mutant was used as a control. (E) TEM analysis of mitochondrial cristae morphology in N mutants. Scale bar: 100 nm. N[55e11] refers to N[55e11]/+ heterozygous females in C-E. (F) Blue native gel (BNG) and WB analyses of RCC assembly in PINK1 and N LOF and GOF backgrounds. Actin and complex IV subunit 1 serve as loading controls. (G) Effects of N GOF on RCC assembly and pS505-dAKT level changes caused by PINK1 LOF. (H, I) Fractionation assay showing enrichment of full-length N at mitochondria (H), and increased mitochondrial N in PINK1-OE condition (I). (J) Co-immunoprecipitation (co-IP) assays using NiGFP fly head tissue to demonstrate N interaction with PINK1 and C-I 30 kD. C-III subunit serves as negative control. (K) Interaction between hNotch1 and PINK1 in the mitochondria of human NSC and GBM cells. C-III subunit serves as negative control. GBM cells show elevated expression of PINK1 and both the full-length and the intracellular domain of Notch1.

We next tested the relationship between N and PINK1 in regulating the mTORC2/AKT axis. As reported before (Clark et al., 2006; Park et al., 2006; Yang et al., 2006), PINK1 LOF altered mitochondrial morphology and impaired indirect flight muscle integrity, as measured by the wing posture assay. These defects were effectively rescued by N GOF (FIG. 3A, 3B). Consistent with N playing an important role in regulating mitochondrial function, N LOF resulted in impaired RCC assembly and reduced ATP production (FIG. 3F, 11A), and as in the case of PINK1, N LOF in DA neurons caused mitochondrial aggregation and neuronal loss (FIG. 11B,11C), features associated with PD (Park et al., 2006; Yang et al., 2006). NB-specific knockdown of RCC-I 75 kD also resulted in reduced NB number at larval stage and loss of DA neurons in surviving adults (FIG. 11D). These results suggested that mitochondrial function regulated by PINK1 and N is important for maintaining the NSCs during development and differentiated DA neurons in adults. Moreover, N mutant mitochondria manifested morphological defects and reduced membrane potential in adult flight muscle (FIG. 3C,3D,3E). Importantly, N GOF efficiently rescued the PINK1 LOF effect on RCC assembly and ATP production, whereas PINK1 GOF failed to rescue the mitochondrial defects caused by N LOF (FIG. 3G, 11A). In keeping with mitochondrial function being a key determinant of mTORC2 activation (Wu et al., 2013), PINK1 and N had similar effects on mTORC2 activity as measured by p-AKT level, and N GOF restored mTORC2 activity in PINK1 LOF condition (FIG. 3G). Intriguingly, PINK1 GOF also restored mTORC2 activity in N LOF condition (FIG. 3G), and the co-activation of PINK1 and N had additive effects on mTORC2 activity (FIG. 12A). Thus, although the functional assays support that N may act downstream of PINK1, the biochemical assays indicate that PINK1 and N have additive effects on mTORC2/AKT activation. PINK1 and N may have signaling branches that act independently to influence mTORC2 activity. Alternatively, PINK1 and N may act at the same level, e.g., by working in a protein complex, rather than in a linear pathway, to regulate mTORC2 activation.

We further explored the mechanisms by which N and PINK1 interact to regulate mitochondrial function. By immunostaining with anti-N, the specificity of which was confirmed using N mutant (FIG. 12B), we found that endogenous N co-localized with the mito-GFP reporter (FIG. 12B) and a N-GFP reporter expressed from the endogenous N promoter colocalized with the mitochondrial marker Tom20 (FIG. 12C). We also found that full-length N was present in Percoll gradient-purified mitochondria, whose purity was confirmed by the absence of various membrane markers (FIG. 3H, 13A), and that N resided mostly at the outer membrane as shown by fractionation studies (FIG. 13B). These results support that N exerts its effect directly at the mitochondrial surface. Mammalian N was also found to localize to mitochondria (FIG. 10D, E).

Given that PINK1 can recruit proteins to mitochondrial surface (Narendra et al., 2010), we next tested whether the mitochondrial localization of N is dependent on PINK1. The amount of mitochondria-bound N, but not total N, was reduced in dPINK1 mutant, but increased in PINK1 GOF condition (FIG. 3I), consistent with PINK1 playing an active role in recruiting N to mitochondria. Intriguingly, although PINK1 can become stabilized on CCCP-damaged mitochondria and recruit proteins such as Parkin to these damaged organelles (Narendra et al., 2010), the amount of mitochondrial N was not affected by damage (FIG. 13E). Importantly, in co-immunoprecipitation assays, PINK1 and N were found to physically associate in vivo (FIG. 3J, 13C). Endogenous N-PINK1 interaction was also observed in human GBM cells (FIG. 3K). Moreover, we detected N association with RCC-I 30 kD subunit, which was previously shown to interact with PINK1 (Wu et al., 2013), but no N association with RCC-III or RCC-IV subunits (FIG. 3J). These results reveal a conserved non-canonical mechanism whereby N regulates mitochondrial function and mTORC2 activity through direct interaction with PINK1 and specific RCC subunit(s) under physiological conditions.

We next tested the relationship between the newly identified non-canonical N signaling pathway and the canonical N pathway in N-directed NB homeostasis. Knocking down the canonical or non-canonical N signaling pathway individually partially rescued N GOF-induced brain tumor phenotype. Combined knockdown of both pathways resulted in near-complete rescue (FIG. 4A, 4B). Strikingly, while RNAi-mediated inhibition of either pathway alone had little effect on normal NB maintenance, their combined knockdown significantly reduced the number of normal NBs (FIG. 4C, 4D), while their combination with control W RNAi had no effect (FIG. 4C, 7C), supporting the importance of both pathways in maintaining normal NBs. Moreover, although the GOF of genes in the non-canonical pathway alone had no obvious effect on NB number, they strongly enhanced NB expansion induced by N GOF (FIG. 4E, 4F). Furthermore, combining the inhibition of mitochondrial fusion regulator Marf (Deng et al., 2008), which impinges on mitochondria and activates the non-canonical pathway (FIG. 13D), with the GOF of dMyc, a key target of the canonical pathway (Song and Lu, 2011), resulted in full rescue of N LOF-induced type II NB loss (FIG. 4G, 4H). In comparison, the co-expression of GFP or Parkin, another gene involved in mitochondrial regulation, failed to modify the rescuing effect of dMyc (FIG. 4H, 13F). Thus, canonical and non-canonical N signaling pathways both play important and specific roles in mediating the effects of N on NSC homeostasis.

Finally, we tested whether co-activation of the canonical and non-canonical N signaling pathways is sufficient to induce ectopic NBs, hence recapitulating the effect of N GOF. Activation of the canonical pathway via Su(H) GOF promoted nucleolar growth of IPs (FIG. 5D), which is likely mediated by dMyc, a known master regulator of nucleolar growth (Song and Lu, 2011). However, no ectopic NB was formed when Su(H) was overexpressed using the IP-specific Erm-Gal4 driver (FIG. 4I, 4J). In contrast, co-expression of Su(H) and AKT-S505D under the control of Erm-Gal4 promoted the dedifferentiation of IPs into ectopic NBs resembling those found in N GOF condition (FIG. 4I, 4J), although AKT-S505D overexpression alone did not affect nucleolar growth (FIG. 5E) and had no obvious effect on type II NB number (FIG. 4I, 4J). Similar results were obtained when Su(H) or Mam were co-expressed with PINK1 (FIG. 14A, 14C). We also used a NΔcdc10 construct defective in Su(H) binding and thus canonical N signaling (Lawrence et al., 2000), but is capable of non-canonical N signaling (FIG. 5A). Co-expression of Su(H) and NΔcdc10 also induced ectopic NBs (FIG. 14B, 14D). These results indicate that non-canonical and canonical N signaling mediate distinct aspects of N function and that they act coordinately to regulate NSC behavior.

Discussion

The results above uncover a novel mechanism of N in regulating NSC self-renewal and maintenance through a non-canonical signaling pathway involving PINK1, mTORC2, and AKT. A central feature of this non-canonical N signaling pathway is specific mitochondrial roles of N in regulating RCC function, through direct interactions with PINK1 and select RCC subunits, and in activating mTORC2. N could act through a number of possible mechanisms, such as facilitating the import or assembly of RCC components (Ades and Butow, 1980), as suggested by its interaction with C-I subunits (FIG. 3J), or directing the quality control of mitochondria as has been implicated for PINK1 (Rugarli and Langer, 2012). Although the exact mechanism remains to be determined, our results will help understand earlier observations in *Drosophila* that mutations in N affected mitochondrial respiration (Thorig et al., 1981), and data from mammalian systems implicating N in mitochondrial and metabolic regulation (Dotti et al., 2004; Landor et al., 2011). The physiological significance of this newly defined non-canonical N pathway is also underscored by the phenotypes of various diseases associated with N dysregulation. Our findings that CSC-like brain tumor-forming cells are particularly dependent on the non-canonical N pathway in flies and humans identify the newly discovered non-canonical N signaling pathway as potential target for disease intervention.

REFERENCES

Ades, I. Z., and Butow, R. A. (1980). The products of mitochondria-bound cytoplasmic polysomes in yeast. *J Biol Chem* 255: 9918-9924.

Andersson, E. R., Sandberg, R., and Lendahl, U. (2011). Notch signaling: simplicity in design, versatility in function. *Development* 138: 3593-3612.

Artavanis-Tsakonas, S., and Muskavitch, M. A. (2010). Notch: the past, the present, and the future. *Curr Top Dev Biol* 92: 1-29.

Bowman, S. K., Rolland, V., Betschinger, J., Kinsey, K. A., Emery, G., and Knoblich, J. A. (2008). The tumor suppressors Brat and Numb regulate transit-amplifying neuroblast lineages in *Drosophila*. *Dev Cell* 14: 535-546.

Cassidy-Stone, A., Chipuk, J. E., Ingerman, E., Song, C., Yoo, C., Kuwana, T., Kurth, M. J., Shaw, J. T., Hinshaw, J. E., Green, D. R., et al. (2008). Chemical inhibition of the mitochondrial division dynamin reveals its role in Bax/Bak-dependent mitochondrial outer membrane permeabilization. *Dev Cell* 14: 193-204.

Clark, I. E., Dodson, M. W., Jiang, C., Cao, J. H., Huh, J. R., Seol, J. H., Yoo, S. J., Hay, B. A., and Guo, M. (2006). *Drosophila* pink1 is required for mitochondrial function and interacts genetically with parkin. *Nature* 441: 1162-1166.

Cloughesy, T. F., Cavenee, W. K., and Mischel, P. S. (2013). Glioblastoma: From Molecular Pathology to Targeted Treatment. *Annu Rev Pathol*.

Deng, H., Dodson, M. W., Huang, H., and Guo, M. (2008). The Parkinson's disease genes pink1 and parkin promote mitochondrial fission and/or inhibit fusion in *Drosophila*. *Proc Natl Acad Sci USA* 105: 14503-14508.

Devine, M. J., Plun-Favreau, H., and Wood, N. W. (2011). Parkinson's disease and cancer: two wars, one front. *Nat Rev Cancer* 11: 812-823.

Dirks, P. B. (2010). Brain tumor stem cells: the cancer stem cell hypothesis writ large. *Mol Oncol* 4: 420-430.

Doe, C. Q. (2008). Neural stem cells: balancing self-renewal with differentiation. *Development* 135: 1575-1587.

Dotti, M. T., De Stefano, N., Bianchi, S., Malandrini, A., Battisti, C., Cardaioli, E., and Federico, A. (2004). A novel NOTCH3 frameshift deletion and mitochondrial abnormalities in a patient with CADASIL. *Arch Neurol* 61: 942-945.

Garcia-Martinez, J. M., Moran, J., Clarke, R. G., Gray, A., Cosulich, S. C., Chresta, C. M., and Alessi, D. R. (2009). Ku-0063794 is a specific inhibitor of the mammalian target of rapamycin (mTOR). *Biochem J* 421: 29-42.

Hietakangas, V., and Cohen, S. M. (2007). Re-evaluating AKT regulation: role of TOR complex 2 in tissue growth. *Genes Dev* 21: 632-637.

Joutel, A., Corpechot, C., Ducros, A., Vahedi, K., Chabriat, H., Mouton, P., Alamowitch, S., Domenga, V., Cecillion, M., Marechal, E., et al. (1996). Notch3 mutations in CADASIL, a hereditary adult-onset condition causing stroke and dementia. *Nature* 383: 707-710.

Knoblich, J. A. (2010). Asymmetric cell division: recent developments and their implications for tumour biology. *Nat Rev Mol Cell Biol* 11: 849-860.

Landor, S. K., Mutvei, A. P., Mamaeva, V., Jin, S., Busk, M., Borra, R., Gronroos, T. J., Kronqvist, P., Lendahl, U., and Sahlgren, C. M. (2011). Hypo- and hyperactivated Notch signaling induce a glycolytic switch through distinct mechanisms. *Proc Natl Acad Sci USA* 108: 18814-18819.

Lawrence, N., Klein, T., Brennan, K., and Martinez Arias, A. (2000). Structural requirements for notch signalling with delta and serrate during the development and patterning of the wing disc of *Drosophila*. *Development* 127: 3185-3195.

Lee, K., Nam, K. T., Cho, S. H., Gudapati, P., Hwang, Y., Park, D. S., Potter, R., Chen, J., Volanakis, E., and Boothby, M. (2012). Vital roles of mTOR complex 2 in Notch-driven thymocyte differentiation and leukemia. *J Exp Med* 209: 713-728.

Liu, C., and Zong, H. (2012). Developmental origins of brain tumors. *Curr Opin Neurobiol* 22: 844-849.

Morrison, S. J., and Kimble, J. (2006). Asymmetric and symmetric stem-cell divisions in development and cancer. *Nature* 441: 1068-1074.

Narendra, D. P., Jin, S. M., Tanaka, A., Suen, D. F., Gautier, C. A., Shen, J., Cookson, M. R., and Youle, R. J. (2010). PINK1 Is Selectively Stabilized on Impaired Mitochondria to Activate Parkin. *PLoS Biol* 8: e1000298.

Park, J., Lee, S. B., Lee, S., Kim, Y., Song, S., Kim, S., Bae, E., Kim, J., Shong, M., Kim, J. M., et al. (2006). Mitochondrial dysfunction in *Drosophila* PINK1 mutants is complemented by parkin. *Nature* 441: 1157-1161.

Perumalsamy, L. R., Nagala, M., and Sarin, A. (2010). Notch-activated signaling cascade interacts with mitochondrial remodeling proteins to regulate cell survival. *Proc Natl Acad Sci USA* 107: 6882-6887.

Rugarli, E. I., and Langer, T. (2012). Mitochondrial quality control: a matter of life and death for neurons. *EMBO J* 31: 1336-1349.

Salmon, P., and Trono, D. (2007). Production and titration of lentiviral vectors. *Curr Protoc Hum Genet* 54: 12.10.1-12.10.24.

Sarbassov, D. D., Guertin, D. A., Ali, S. M., and Sabatini, D. M. (2005). Phosphorylation and regulation of Akt/PKB by the rictor-mTOR complex. *Science* 307: 1098-1101.

Song, Y., and Lu, B. (2011). Regulation of cell growth by Notch signaling and its differential requirement in normal vs. tumor-forming stem cells in *Drosophila*. *Genes Dev* 25: 2644-2658.

Sousa-Nunes, R., Cheng, L. Y., and Gould, A. P. (2010). Regulating neural proliferation in the *Drosophila* CNS. *Curr Opin Neurobiol* 20: 50-57.

Thorig, G. E., Heinstra, P. W., and Scharloo, W. (1981). The action of the notchlocus in *Drosophila melanogaster*. II. Biochemical effects of recessive lethals on mitochondrial enzymes. *Genetics* 99: 65-74.

Wang, H., Somers, G. W., Bashirullah, A., Heberlein, U., Yu, F., and Chia, W. (2006). Aurora-A acts as a tumor suppressor and regulates self-renewal of *Drosophila* neuroblasts. *Genes Dev* 20: 3453-3463.

Weng, A. P., Ferrando, A. A., Lee, W., Morris, J. P. t., Silverman, L. B., Sanchez-Irizarry, C., Blacklow, S. C., Look, A. T., and Aster, J. C. (2004). Activating mutations of NOTCH1 in human T cell acute lymphoblastic leukemia. *Science* 306: 269-271.

Weng, M., Golden, K. L., and Lee, C. Y. (2010). dFezf/Earmuff maintains the restricted developmental potential of intermediate neural progenitors in Drosophila. *Dev Cell* 18: 126-135.

Wu, Z., Sawada, T., Shiba, K., Liu, S., Kanao, T., Takahashi, R., Hattori, N., Imai, Y., and Lu, B. (2013). Tri-cornered/NDR kinase signaling mediates PINK1-directed mitochondrial quality control and tissue maintenance. *Genes Dev* 27: 157-162.

Yang, Y., Gehrke, S., Imai, Y., Huang, Z., Ouyang, Y., Wang, J. W., Yang, L., Beal, M. F., Vogel, H., and Lu, B. (2006). Mitochondrial pathology and muscle and dopaminergic neuron degeneration caused by inactivation of Drosophila Pink1 is rescued by Parkin. *Proc Natl Acad Sci USA* 103: 10793-10798.

Zhong, W., and Chia, W. (2008). Neurogenesis and asymmetric cell division. *Curr Opin Neurobiol* 18: 4-11.

Zoncu, R., Efeyan, A., and Sabatini, D. M. (2011). mTOR: from growth signal integration to cancer, diabetes and ageing. *Nat Rev Mol Cell Biol* 12: 21-35.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of the present invention is embodied by the appended claims.

That which is claimed is:

1. A method of treating an individual for a brain tumor or a hematological malignancy, the method comprising:
administering to the individual an inhibitor of a member of a non-canonical Notch signaling pathway that includes Notch and a protein that promotes mitochondrial development or function in an amount effective to treat the brain tumor or hematological malignancy.

2. The method according to claim 1, wherein the protein that promotes mitochondrial development or function is expressed by a gene selected from a mitochondrial quality control gene, a respiratory chain complex gene, mitochondrial fission gene, and the mitochondrial biogenesis gene.

3. The method according to claim 1, wherein the protein that promotes mitochondrial development or function is selected from PTEN-induced putative kinase 1 (PINK1), RCC-I (respiratory chain complex I) 75 kD subunit (ND-75), Dynamin-related protein 1 (Drp1), and Peroxisome proliferator-activated receptor gamma coactivator 1-alpha (PGC-1α).

4. The method according to claim 1, wherein the method is a method for treating an individual for a brain tumor.

5. The method according to claim 1, wherein the method is a method for treating an individual for a hematological malignancy.

6. The method according to claim 5, wherein the hematological malignancy is T-cell acute lymphoblastic leukemia (T-ALL).

7. The method according to claim 4, wherein the brain tumor is glioblastoma multiforme (GBM).

8. The method according to claim 4, further comprising determining if the individual has a Notch-associated cancer, and administering the inhibitor based on the determination.

9. The method according to claim 1, further comprising detecting a reduction of proliferation of the brain tumor cells or hematological malignancy cells, wherein a reduction in the proliferation indicates that the brain tumor or hematological malignancy is treated.

10. The method according to claim 1, wherein the inhibitor targets Drp1, mTOR or mitochondrial complex I.

11. The method according to claim 10, wherein the inhibitor is selected from Mdivi-1, Ku-0063794 and rotenone.

SEQUENCE LISTING

<160> NUMBER OF SEQ ID NOS: 2

<210> SEQ ID NO 1
<211> LENGTH: 21
<212> TYPE: DNA
<213> ORGANISM: Artificial sequence
<220> FEATURE:
<223> OTHER INFORMATION: shRNA

<400> SEQUENCE: 1
tagatgaagc acatttgcgg c                                             21

<210> SEQ ID NO 2
<211> LENGTH: 21
<212> TYPE: DNA
<213> ORGANISM: Artificial sequence
<220> FEATURE:
<223> OTHER INFORMATION: shRNA

<400> SEQUENCE: 2
tatcagatac tcctccagcc g                                             21

12. The method according to claim 11, wherein the inhibitor is Mdivi-1.

13. The method according to claim 11, wherein the inhibitor is Ku-0063794.

14. The method according to claim 11, wherein the inhibitor is rotenone.

15. The method according to claim 1, wherein the pathway comprises Notch, PINK1, and at least one RCC-I subunit, rapamycin complex 2 (mTORC2), and protein kinase B (AKT).

16. The method according to claim 1, wherein the pathway comprises Notch and PINK1.

17. The method according to claim 1, wherein the pathway comprises Notch and at least one RCC-I subunit.

18. The method according to claim 1, wherein the pathway comprises Notch and mTORC2.

19. The method according to claim 1, wherein the pathway comprises Notch and AKT.

20. The method according to claim 1, wherein the inhibitor targets PTEN-induced putative kinase 1 (PINK1).

21. The method according to claim 1, wherein the inhibitor targets RCC-I (respiratory chain complex I) 75 kD subunit (ND-75).

22. The method according to claim 1, wherein the inhibitor targets Dynamin-related protein 1 (Drp1).

23. The method according to claim 1, wherein the inhibitor targets Peroxisome proliferator-activated receptor gamma coactivator 1-alpha (PGC-1α).

* * * * *